US007619746B2

(12) United States Patent  
De Lega

(10) Patent No.: US 7,619,746 B2  
(45) Date of Patent: Nov. 17, 2009

(54) GENERATING MODEL SIGNALS FOR INTERFEROMETRY

(75) Inventor: Xavier Colonna De Lega, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 101 days.

(21) Appl. No.: 11/780,360

(22) Filed: Jul. 19, 2007

(65) Prior Publication Data

US 2009/0021723 A1  Jan. 22, 2009

(51) Int. Cl.  
*G01B 11/02* (2006.01)

(52) U.S. Cl. .................................................. 356/511

(58) Field of Classification Search ................ 356/497, 356/503–504, 511–514  
See application file for complete search history.

(56) References Cited

U.S. PATENT DOCUMENTS

| 2,612,074 A | 9/1952 | Mirau |
| 4,188,122 A | 2/1980 | Massie et al. |
| 4,199,219 A | 4/1980 | Suzuki et al. |
| 4,340,306 A | 7/1982 | Balasubramanian |
| 4,355,903 A | 10/1982 | Sandercock |
| 4,523,846 A | 6/1985 | Breckinridge et al. |
| 4,576,479 A | 3/1986 | Downs |
| 4,583,858 A | 4/1986 | Lebling et al. |
| 4,618,262 A | 10/1986 | Maydan et al. |
| 4,639,139 A | 1/1987 | Wyant et al. |
| 4,660,980 A | 4/1987 | Takabayashi et al. |
| 4,710,642 A | 12/1987 | McNeil |
| 4,806,018 A | 2/1989 | Falk |
| 4,818,110 A | 4/1989 | Davidson |
| 4,869,593 A | 9/1989 | Biegen |
| 4,923,301 A | 5/1990 | White |
| 4,948,253 A | 8/1990 | Biegen |
| 4,964,726 A | 10/1990 | Kleinknecht et al. |
| 4,999,014 A | 3/1991 | Gold et al. |
| 5,042,949 A | 8/1991 | Greenberg et al. |
| 5,042,951 A | 8/1991 | Gold et al. |
| 5,073,018 A | 12/1991 | Kind et al. |
| 5,112,129 A | 5/1992 | Davidson et al. |

(Continued)

FOREIGN PATENT DOCUMENTS

DE    4108944    9/1992

(Continued)

OTHER PUBLICATIONS

C. Akcay et al., "Spectral shaping to improve the point spread function in optical coherence tomography", *Optics Letters*, vol. 28 No. 20, pp. 1921-1923 (Oct. 15, 2003).

(Continued)

*Primary Examiner*—Michael A Lyons  
(74) *Attorney, Agent, or Firm*—Fish & Richardson P.C.

(57) ABSTRACT

A method is disclosed which includes, for each of multiple areas of a test surface on a test object having different reflectivities, using an interferometry system to measure each area in a first mode of operation that measures information about the reflectivity of the area over a range of angles and wavelengths; using the same interferometry-system to measure the test surface in a second mode of operation that interferometrically profiles a topography of the test surface over a range including at least some of the multiple areas; and correcting the profile based on the information about the reflectivity of the multiple areas to reduce errors.

54 Claims, 18 Drawing Sheets

U.S. PATENT DOCUMENTS

| | | | |
|---|---|---|---|
| 5,129,724 | A | 7/1992 | Brophy et al. |
| 5,133,601 | A | 7/1992 | Cohen et al. |
| 5,135,307 | A | 8/1992 | De Groot et al. |
| 5,153,669 | A | 10/1992 | DeGroot |
| 5,164,790 | A | 11/1992 | McNeil et al. |
| 5,166,751 | A | 11/1992 | Massig |
| 5,173,746 | A | 12/1992 | Brophy |
| 5,194,918 | A | 3/1993 | Kino et al. |
| 5,241,369 | A | 8/1993 | McNeil et al. |
| 5,301,010 | A | 4/1994 | Jones et al. |
| 5,355,221 | A | 10/1994 | Cohen et al. |
| 5,384,717 | A | 1/1995 | Ebenstein |
| 5,386,119 | A | 1/1995 | Ledger |
| 5,390,023 | A | 2/1995 | Biegen |
| 5,398,113 | A | 3/1995 | De Groot |
| 5,402,234 | A | 3/1995 | Deck |
| 5,459,564 | A | 10/1995 | Chivers |
| 5,471,303 | A | 11/1995 | Ai et al. |
| 5,481,811 | A | 1/1996 | Smith |
| 5,483,064 | A | 1/1996 | Frey et al. |
| 5,539,517 | A | 7/1996 | Cabib et al. |
| 5,543,841 | A | 8/1996 | Kanamori |
| 5,555,471 | A | 9/1996 | Xu et al. |
| 5,587,792 | A | 12/1996 | Nishizawa et al. |
| 5,589,938 | A | 12/1996 | Deck |
| 5,602,643 | A | 2/1997 | Barrett |
| 5,633,714 | A | 5/1997 | Nyyssonen |
| 5,640,270 | A | 6/1997 | Aziz et al. |
| 5,703,692 | A | 12/1997 | McNeil et al. |
| 5,757,502 | A | 5/1998 | Weling |
| 5,774,224 | A | 6/1998 | Kerstens |
| 5,777,740 | A | 7/1998 | Lacey et al. |
| 5,777,742 | A | 7/1998 | Marron |
| 5,784,164 | A | 7/1998 | Deck et al. |
| 5,856,871 | A | 1/1999 | Cabib et al. |
| 5,867,276 | A | 2/1999 | McNeil et al. |
| 5,880,838 | A | 3/1999 | Marx et al. |
| 5,900,633 | A | 5/1999 | Solomon et al. |
| 5,912,741 | A | 6/1999 | Carter et al. |
| 5,923,423 | A | 7/1999 | Sawarti et al. |
| 5,943,134 | A | 8/1999 | Yamaguchi et al. |
| 5,953,124 | A | 9/1999 | Deck |
| 5,956,141 | A | 9/1999 | Hayashi |
| 5,959,735 | A | 9/1999 | Maris et al. |
| 5,963,329 | A | 10/1999 | Conrad et al. |
| 6,028,670 | A | 2/2000 | Deck |
| 6,160,621 | A | 12/2000 | Perry et al. |
| 6,172,452 | B1 | 1/2001 | Itaya et al. |
| 6,242,739 | B1 | 6/2001 | Cherkassky |
| 6,249,351 | B1 | 6/2001 | de Groot |
| H1972 | H | 7/2001 | Inoue |
| 6,259,521 | B1 | 7/2001 | Miller et al. |
| 6,275,297 | B1 | 8/2001 | Zalicki |
| 6,377,349 | B1 | 4/2002 | Fercher |
| 6,381,009 | B1 | 4/2002 | McGahan |
| 6,392,749 | B1 | 5/2002 | Meeks et al. |
| 6,417,109 | B1 | 7/2002 | Jordan et al. |
| 6,429,943 | B1 | 8/2002 | Opsal et al. |
| 6,449,048 | B1 | 9/2002 | Olszak |
| 6,449,066 | B1 | 9/2002 | Arns et al. |
| 6,483,580 | B1 | 11/2002 | Xu et al. |
| 6,500,591 | B1 | 12/2002 | Adams |
| 6,507,405 | B1 | 1/2003 | Grek et al. |
| 6,525,825 | B2 | 2/2003 | de Groot et al. |
| 6,545,761 | B1 | 4/2003 | Aziz et al. |
| 6,545,763 | B1 | 4/2003 | Kim et al. |
| 6,590,656 | B2 | 7/2003 | Xu et al. |
| 6,597,460 | B2 | 7/2003 | Groot et al. |
| 6,611,330 | B2 | 8/2003 | Lee et al. |
| 6,624,894 | B2 | 9/2003 | Olszak et al. |
| 6,633,389 | B1 | 10/2003 | Poris et al. |
| 6,633,831 | B2 | 10/2003 | Nikoonahad et al. |
| 6,636,322 | B1 | 10/2003 | Terashita |
| 6,694,284 | B1 | 2/2004 | Nikoonahad et al. |
| 6,714,307 | B2 | 3/2004 | De Groot et al. |
| 6,721,094 | B1 | 4/2004 | Sinclair et al. |
| 6,741,357 | B2 | 5/2004 | Wang et al. |
| 6,741,360 | B2 | 5/2004 | D'Agraives et al. |
| 6,775,006 | B2 | 8/2004 | De Groot et al. |
| 6,775,009 | B2 | 8/2004 | Hill |
| 6,798,511 | B1 | 9/2004 | Zhan et al. |
| 6,822,745 | B2 | 11/2004 | De Groot et al. |
| 6,856,384 | B1 | 2/2005 | Rovira |
| 6,888,638 | B1 | 5/2005 | Hill |
| 6,891,627 | B1 | 5/2005 | Levy et al. |
| 6,909,509 | B2 | 6/2005 | DeGroot |
| 6,925,860 | B1 | 8/2005 | Poris et al. |
| 6,940,604 | B2 | 9/2005 | Jung et al. |
| 6,956,658 | B2 | 10/2005 | Meeks et al. |
| 6,956,660 | B2 | 10/2005 | Meeks et al. |
| 6,985,232 | B2 | 1/2006 | Sezginer |
| 6,989,905 | B2 | 1/2006 | De Groot |
| 6,999,180 | B1 | 2/2006 | Janik et al. |
| 7,012,700 | B2 | 3/2006 | de Groot et al. |
| 7,018,271 | B2 | 3/2006 | Wiswesser et al. |
| 7,038,850 | B2 | 5/2006 | Chang et al. |
| 7,046,371 | B2 | 5/2006 | De Lega et al. |
| 7,061,623 | B2 | 6/2006 | Davidson |
| 7,068,376 | B2 | 6/2006 | De Groot |
| 7,088,451 | B2 | 8/2006 | Sezginer |
| 7,102,761 | B2 | 9/2006 | De Lega et al. |
| 7,106,454 | B2 | 9/2006 | De Groot et al. |
| 7,119,909 | B2 | 10/2006 | Unruh et al. |
| 7,139,081 | B2 | 11/2006 | De Groot |
| 7,139,083 | B2 | 11/2006 | Fielden et al. |
| 7,142,311 | B2 | 11/2006 | De Lega |
| 7,177,030 | B2 | 2/2007 | Leizerson |
| 7,205,518 | B2 | 4/2007 | Neuvonen |
| 7,239,398 | B2 | 7/2007 | De Groot et al. |
| 7,271,918 | B2 | 9/2007 | De Groot et al. |
| 7,283,248 | B2 | 10/2007 | Hill |
| 7,289,225 | B2 | 10/2007 | De Groot |
| 7,298,494 | B2 | 11/2007 | De Groot |
| 7,304,747 | B2 | 12/2007 | De Lega |
| 7,315,382 | B2 | 1/2008 | De Groot |
| 7,324,210 | B2 | 1/2008 | De Groot et al. |
| 7,324,214 | B2 | 1/2008 | De Groot et al. |
| 7,428,057 | B2 * | 9/2008 | De Lega et al. ............ 356/511 |
| 2002/0015146 | A1 | 2/2002 | Meeks et al. |
| 2002/0135775 | A1 | 9/2002 | de Groot et al. |
| 2002/0148955 | A1 | 10/2002 | Hill |
| 2002/0196450 | A1 | 12/2002 | Olszak et al. |
| 2003/0011784 | A1 | 1/2003 | de Groot et al. |
| 2003/0048458 | A1 | 3/2003 | Mieher et al. |
| 2003/0075721 | A1 | 4/2003 | Li |
| 2003/0112444 | A1 | 6/2003 | Yang et al. |
| 2003/0137671 | A1 | 7/2003 | De Groot et al. |
| 2003/0197871 | A1 | 10/2003 | De Groot |
| 2004/0027576 | A1 | 2/2004 | De Groot et al. |
| 2004/0075843 | A1 | 4/2004 | Marron et al. |
| 2004/0085544 | A1 | 5/2004 | de Groot et al. |
| 2004/0185582 | A1 | 9/2004 | Kueny |
| 2004/0189999 | A1 | 9/2004 | de Groot et al. |
| 2004/0233442 | A1 | 11/2004 | Mieher et al. |
| 2004/0233444 | A1 | 11/2004 | Mieher et al. |
| 2004/0246493 | A1 | 12/2004 | Kim et al. |
| 2005/0024773 | A1 | 2/2005 | Lille |
| 2005/0057757 | A1 | 3/2005 | de Lega et al. |
| 2005/0068540 | A1 | 3/2005 | de Groot et al. |
| 2005/0073692 | A1 | 4/2005 | de Groot et al. |
| 2005/0078318 | A1 | 4/2005 | de Groot |
| 2005/0078319 | A1 | 4/2005 | de Groot |
| 2005/0088663 | A1 | 4/2005 | de Groot et al. |
| 2005/0146727 | A1 | 7/2005 | Hill |

| | | | |
|---|---|---|---|
| 2005/0179911 A1 | 8/2005 | Boomgarden et al. |
| 2005/0225769 A1 | 10/2005 | Bankhead et al. |
| 2005/0237534 A1 | 10/2005 | Deck |
| 2005/0237537 A1 | 10/2005 | Leizerson et al. |
| 2006/0012582 A1 | 1/2006 | de Lega |
| 2006/0072104 A1 | 4/2006 | Engel et al. |
| 2006/0119841 A1 | 6/2006 | Saunders et al. |
| 2006/0158657 A1 | 7/2006 | de Lega et al. |
| 2006/0158658 A1 | 7/2006 | de Lega et al. |
| 2006/0158659 A1 | 7/2006 | de Lega et al. |
| 2006/0170932 A1 | 8/2006 | Hayashi et al. |
| 2006/0187465 A1 | 8/2006 | De Groot |
| 2006/0262321 A1 | 11/2006 | De Groot |
| 2007/0008551 A1 | 1/2007 | Tang |
| 2007/0046953 A1 | 3/2007 | de Groot et al. |
| 2007/0081167 A1 | 4/2007 | De Groot et al. |
| 2007/0086013 A1 | 4/2007 | De Lega et al. |
| 2007/0091317 A1 | 4/2007 | Freischlad et al. |
| 2007/0091318 A1 | 4/2007 | Freischlad et al. |
| 2007/0091940 A1 | 4/2007 | Jameson |
| 2007/0097380 A1 | 5/2007 | De Groot et al. |
| 2007/0127036 A1 | 6/2007 | Liao et al. |
| 2007/0139656 A1 | 6/2007 | Wan |
| 2007/0247637 A1 | 10/2007 | De Groot |
| 2008/0018901 A1 | 1/2008 | de Groot |
| 2008/0088849 A1 | 4/2008 | de Lega et al. |
| 2008/0174784 A1 | 7/2008 | de Lega et al. |

FOREIGN PATENT DOCUMENTS

| | | |
|---|---|---|
| DE | 4309056 | 9/1994 |
| EP | 0 397 388 A2 | 11/1990 |
| EP | 0 549 166 A2 | 6/1993 |
| EP | 0 617 255 A1 | 9/1994 |
| EP | 0 929 094 A2 | 7/1999 |
| GB | 2385417 | 8/2003 |
| JP | 8327327 | 12/1996 |
| JP | 09-218016 | 8/1997 |
| JP | 2000121317 | 4/2000 |
| JP | 2000-180124 | 6/2000 |
| JP | 2001-141652 | 5/2001 |
| JP | 2001-272603 | 10/2001 |
| JP | 2007147620 | 6/2007 |
| KR | 20000061037 | 10/2000 |
| WO | WO 93/24805 | 12/1993 |
| WO | WO 95/09343 | 4/1995 |
| WO | WO 97/44633 | 11/1997 |
| WO | WO 02/082008 | 10/2002 |
| WO | WO 03/036229 | 5/2003 |
| WO | WO 03/062802 | 7/2003 |
| WO | WO 2004/023071 | 3/2004 |
| WO | WO 2005/029192 | 3/2005 |

OTHER PUBLICATIONS

R.M.A. Azzam et al., "Reflection and Transmission of Polarized Light by Stratified Planar Structures", *Ellipsometry and Polarized Light*, Elsevier Science B.V. ISBN 0 444 87016 4 (Paperback) pp. 267-363 (1987).

M. Bashkansky et al., "Signal Processing for Improving Field Cross-correlation Function in Optical Coherence Tomography", *Supplement to Optics & Photonics News*, 9(5) (May 1998).

A. Bosseboeuf et al., "Application of microscopic interferometry techniques in the MEMS field", *Proceedings of SPIE*, vol. 5145, pp. 1-16 (2003).

M. Davidson et al., "An Application of Interference Microscopy to Integrated Circuit Inspection and metrology", *Proceedings SPIE*, vol. 775, pp. 233-247 (1987).

T. Dresel et al., "Three-dimensional sensing of rough surfaces by coherence radar", *Applied Optics*, vol. 31, No. 7, pp. 919-925 (Mar. 1, 1992).

J.E. Greivenkamp, "Generalized data reduction for heterodyne interferometry", *Optical Engineering.*, vol. 23 No. 4, pp. 350-352 (Jul./Aug. 1984).

P. de Groot et al., "Signal modeling for low coherence height-scanning interference microscopy", *Applied Optics*, vol. 43 No. 25, pp. 4821-4830 (Sep. 1, 2004).

P. de Groot, "Derivation of algorithms for phase-shifting interferometry using the concept of a data-sampling window", *Appl. Opt.*, 34(22), p. 4723-4730 (1995).

P. de Groot et al., "Signal modeling for modern interference microscopes", *SPIE Proceedings*, 5457-4 (2004).

Peter de Groot et al., "Determination of fringe order in white-light interference microscopy", *Appl. Opt.*, 41(22) pp. 4571-4578 (2002).

Feke, Gilbert D. et al., "Interferometric back focal plane microellipsometry", *Applied Optics*, vol. 37, No. 10, pp. 1796-1802 (Apr. 1, 1998).

P.A. Flournoy et al., "White-light interferometric thickness gauge", *Appl. Opt.*, 11(9), pp. 1907-1915 (1972).

G. Hausler et al., "Coherence Radar and Spectral Radar—New Tools for Dermatological Diagnosis", *Journal of Biomedical Optics*, vol. 3, No. 1, pp. 21-31 (Jan. 1998).

R.D. Holmes et al., "Scanning microellipsometry for extraction of true topography", *Electronics Letters*, vol. 31, No. 5, pp. 358-359 (Mar. 2, 1995).

Kim, Seung-Woo et al., "Thickness-profile measurement of transparent thin-film layers by white-light scanning interferometry", *Applied Optics*, vol. 38, No. 28, pp. 5968-5973 (Oct. 1, 1999).

Kino, Gordon S. et al., "Mirau correlation microscope", *Applied Optics*, vol. 29, No. 26, pp. 3775-3783 (Sep. 10, 1990).

Kieran G. Larkin, "Efficient nonlinear algorithm for envelope detection in white light interferometry", *Journal of the Optical Society of America A*, vol. 13, No. 4, pp. 832-843 (1996).

Kujawinska, Malgorzata, "Spatial Phase Measurement Methods", *Interferogram Analysis: Digital Fringe Pattern Measurement Techniques*, IOP Publishing Ltd. 1993, pp. 141-193.

Lee et al., "Profilometry with a coherence scanning microscope", *Appl. Opt.*, 29(26), pp. 3784-3788 (1990).

I. Lee-Bennett, "Advances in non-contacting surface metrology", *OF&T Workshop*, papter OTuC1 (2004).

K. Leonhardt et al., "Micro-Ellipso-Height-Profilometry", *Optics Communications*, vol. 80, No. 3, 4, pp. 205-209 (Jan. 1, 1991).

Y. Liu et al., "Common path interferometric microellipsometry", *SPIE*, vol. 2782, pp. 635-645 (1996).

Lyakin et al., "The interferometric system with resolution better than coherence length for determination of geometrical thickness and refractive index of a layer object", *Proceedings of the SPIE—The International Society for Optical Engineering SPIE-INT. Soc. Opt. Eng USA*, vol. 4956, pp. 163-169 (Jul. 2003).

C.J. Morgan, "Least-Squares estimation in phase-measurement interferometry", *Optics Letters*, 7(8), pp. 368-370 (1982).

Ngoi et al., "Phase-shifting interferometry immune to vibration", *Applied Optics*, vol. 40, No. 19, pp. 3211-3214 (2001).

A.V. Oppenheim et al., "10.3: The time-dependent Fourier Transform", *Discrete-Time Signal Processing*, $2^{nd}$ Edition, pp. 714-722 (Prentice Hall, New Jersey, 1999).

M.C. Park et al., "Direct quadratic polynomial fitting for fringe peak detection of white light scanning interferograms", *Optical Engineering*, vol. 39, No. 4, pp. 952-959 (2000).

S. Pettigrand et al., "Mesures 3D de topographies et de vibrations a l'echelle (sub)micrometrique par microscopie optique interferometrique", *Proc. Club CMOI, Methodes et Techniques Optiques pour l'Industrie*, (2002).

M. Pluta, "Advanced light microscopy", vol. 3, PWN—Polish Scientific Publishers (Elsevier, Amsterdam), pp. 265-271 (1993).

W.H. Press et al., "Linear Correlation", *Numerical Recipes in C*, Cambridge University Press, $2^{nd}$ Edition, pp. 636-639 (1992).

Rosencwaig, Allan et al., "Beam profile reflectometry: A new technique for dielectric film measurements", *Applied Physics Letters*, vol. 60, No. 11, pp. 1301-1303 (Mar. 16, 1992).

P. Sandoz et al., "Optical implementation of frequency domain analysis for white light interferometry", *Proceedings SPIE*, vol. 2545, pp. 221-228 (Jun. 1995).

P. Sandoz et al., "High-resolution profilometry by using phase calculation algorithms for spectroscopic analysis of white-light interferograms", *Journal of Modern Optics*, vol. 43, No. 4, pp. 701-708 (1996).

Sandoz, Patrick "Wavelet transform as a processing tool in white-light interferometry", *Optics Letters*, vol. 22, No. 14, pp. 1065-1067 (Jul. 15, 1997).

P. Sandoz et al., "Processing of white light correlograms: simultaneous phase and envelope measurements by wavelet transformation", *SPIE*, vol. 3098, pp. 73-82 (1997).

U. Schnell et al., "Dispersive white-light interferometry for absolute distance measurement with dielectric multilayer systems on the target", *Optics Letters*, vol. 21, No. 7, pp. 528-530 (Apr. 1996).

J. Schwider et al., "Dispersive interferometric profilometer", *Optics Letters*, vol. 19, No. 13, pp. 995-997 (Jul. 1994).

C.W. See et al., "Scanning optical microellipsometer for pure surface profiling", *Applied Optics*, vol. 35, No. 34, pp. 6663-6668 (Dec. 1, 1996).

Shatalin, S.V. et al., "Reflection conoscopy and micro-ellipsometry of isotropic thin film structures", *Journal of Microscopy*, vol. 179, Part 3, pp. 241-252 (Sep. 1995).

M. Totzeck, "Numerical simulation of high-NA quantitative polarization microscopy and corresponding near-fields", *Optik*, vol. 112, No. 9, pp. 399-406 (2001).

R. Tripathi et al., "Spectral shaping for non-Gaussian source spectra in optical coherence tomography", *Optics Letters*, vol. 27, No. 6, pp. 406-408 (Mar. 15, 2002).

D. Willenborg et al, "A novel micro-spot dielectric film thickness measurement system", *SPIE*, vol. 1594, pp. 322-333 (1991).

International Search Report for International Application No. PCT/US2006/001740 dated Jun. 6, 2006 by Authorized Officer Sibylle Schubert-Püschel.

7,151,607 Dec. 19, 2006 De Groot et al.

Abdulhalim, "Spectroscopic interference microscopy technique for measurement of layer parameters", Meas. Sci. Technol., vol. 12, pp. 1996-2001 (2001).

Biegen, "Determination of the Phase Change on Reflection from Two-beam Interference," Optics Letters, 19:21:1690-1692, Nov. 1, 1994.

Bishop, et al., "Grating line shape characterization using scatterometry," SPIE 1545, 64-73 (1991).

Chim, et al., "Three-Dimensional Image Realization in Interference Microscopy", Applied Optics, May 10, 1992, vol. 31, No. 14.

Creath, "Step height measurement using two-wavelength phase-shifting interferometry", Applied Optics, vol. 26, No. 14, pp. 2810-2816 (Jul. 15, 1987).

Danielson et al., "Absolute Optical Ranging Using Low Coherence Interferometry," Applied Optics, 30:21:2975-2979, Jul. 20, 1991.

de Groot et al., "Angle-resolved three-dimensional analysis of surface films by coherence scanning interferometry", Optics Letters, vol. 32, No. 12, pp. 1638-1640 (Jun. 15, 2007).

de Groot et al.; "Three-dimensional imaging by sub-Nyquist sampling of white-light interfergrams"; Optics Letters vol. 18, No. 17; pp. 1462-1464, Sep. 1, 1993.

de Groot, "Extending the unambiguous range of two-color interferometers", Applied Optics, vol. 33, No. 25, pp. 5948-5953 (Sep. 1, 1994).

de Groot, "Three-color laser-diode interferometer", Applied Optics, vol. 30, No. 25, pp. 3612-3616 (Sep. 1, 1991).

de Groot, P., "Phase-shift calibration errors in interometers with spherical Fizeua cavities," Applied Optics, vol. 34:16, pp. 2856-2863 (Jun. 1, 1995).

de Lega, X., et al., "Optical topography measurement of patterned wafers," American Institute of Physics Conference Proceedings, vol. 788, pp. 432-436 (2005).

Debnath, S.K., et al., "Spectrally resolved phase-shifting interferometry of transparent thin films: sensitivity of thickness measurements," Appl. Opt. 45, 34 8636-8640 (2006).

Deck et al., "Two-color light-emitting-diode source for high-precision phase-shifting interferometry", Optics Letters, vol. 18, No. 22, pp. 1899-1901 (Nov. 15, 1993).

Gale et al., "Linnik microscope imaging of integrated circuit structures", Applied Optics vol. 35, No. 1, pp. 131-148 (Jan. 1, 1996).

Ghiglia et al., "Quality-Guided Path Following", Two-Dimensional Phase Unwrapping—Theory, Algorithms and Software, John Wiley & Sons publishers, ISBN 0-471-24935-1, pp. 122-136 (1998).

Hecht, "Basics of Coherence Theory," Optics, 2nd Ed., Addison Wesley, pp. 516-517 (1987).

Kleinknecht, et al., "Linewidth measurement on IC masks and wafers by grating test patterns," Appl. Opt. 19(4), 523-533 (1980).

Kohlhaas, et al., "High-Resolution OCDR for Testing Integrated-Optical Waveguides: Dispersion-Corrupted Experimental Data Corrected by a Numerical Algorithm", Journal of Lightwave Technology, Nov. 1991, vol. 9, No. 11.

Naqvi, et al., "Linewidth measurement of gratings on photomasks: a simple technique," Appl. Opt., 31(10), 1377-1384 (1992).

Novak et al., "Template-based software for accurate MEMS characterization", Proceedings of SPIE, Fol. 4980, pp. 75-80 (2003).

Onodera et al., "Two-wavelength interferometry that uses a Fourier-transform method", Applied Optics, vol. 37, No. 34, pp. 7988-7994 (Dec. 1, 1998).

Peng, S.T., et al., "Theory of Periodic Dielect Waveguides," IEEE Trans Microwave Theory and Technique MTT-23(1), 123-133 (1975).

Pfortner et al., "Red-green-blue interferometer for the metrology of discontinuous structures", Applied Optics, vol. 42, No. 4, pp. 667-673 (Feb. 1, 2003).

Raymond, C.J., "Scatterometry for Semiconductor Metrology," in Handbook of silicon semiconductor metrology, A.J. Diebold, Ed. (Marcel Dekker, Inc., New York 2001).

Raymond, et al., "Scatterometry for CD measurements of etched structures," SPIE 2725, 720-728 (1996).

Schmit, J. et al., "Extended averaging technique for derivation of error-compensating algorithms in phase-shifting interferometry," Applied Optics, vol. 34:19, pp. 3610-3619 (Jul. 1, 1995).

Sheppard et al., "Effect of numerical aperture on interference fringe spacing", Applied Optics, vol. 34, No. 22, pp. 4731-4734 (Aug. 1, 1995).

Tzannes et al., Measurement of the modulation transfer function of infrared cameras, Optical Engineering, vol. 34, No. 6, pp. 1808-1817 (Jun. 1995). cited by other.

Wyant, "Phase shifting interferometry" (1998).

Youngquist, et al., "Optical Coherence-Domain Reflectometry: a New Optical Evaluation Technique", Optical Letters, Mar. 1987, vol. 12, No. 3.

Zhan, Q., et al., "Measurement of surface features beyond the diffraction limit with an imaging ellipsometer," Opt. Lett. 27, 821-823 (2002).

PCT Search Report dated Jun. 10, 2008 by ISA/RO.

International Search Report corresponding to International Appln. No. PCT/US2008/69945, dated Dec. 18, 2008.

R.M.A. Azzam et al, "Ellipsometric function of a film-substrate system: Applications to the design of reflection-type optical devices and to ellipsometry", Journal of the Optical Society of America, vol. 5, No. 3, pp. 252-260 (1975).

Berman et al., "Review of In Situ & In-line Detection for CMP Applications", *Semiconductor Fabtech—8th Edition*, pp. 267-274 (1998).

* cited by examiner

— SIGNAL INTENSITY

— SPECTRAL MAGNITUDE
---- SPECTRAL PHASE

GENERATING MODEL SIGNALS FOR INTERFEROMETRY

BACKGROUND

The invention relates to interferometry.

Interferometric techniques are commonly used to measure the profile of a surface of an object. To do so, an interferometer combines a measurement wavefront reflected from the surface of interest with a reference wavefront reflected from a reference surface to produce an interferogram. Fringes in the interferogram are indicative of spatial variations between the surface of interest and the reference surface.

A scanning interferometer scans the optical path length difference (OPD) between the reference and measurement legs of the interferometer over a range comparable to, or larger than, the coherence length of the interfering wavefronts, to produce a scanning interferometry signal for each camera pixel used to measure the interferogram. A limited coherence length can he produced, for example, by using a white-light source, which is referred to as scanning white light interferometry (SWLI). A typical scanning white light interferometry (SWLI) signal is a few fringes localized near the zero optical path difference (OPD) position. The signal is typically characterized by a sinusoidal carrier modulation (the "fringes") with bell-shaped fringe-contrast envelope. The conventional idea underlying SWLI metrology is to make use of the localization of the fringes to measure surface profiles.

SWLI processing techniques include two principle trends. The first approach is to locate the peak or center of the envelope, assuming that this position corresponds to the zero optical path difference (OPD) of a two-beam interferometer for which one beam reflects from the object surface. The second approach is to transform the signal into the frequency domain and calculate the rate of change of phase with wavelength, assuming that an essentially linear slope is directly proportional to object position. See, for example, U.S. Pat. No. 5,398,113 to Peter de Groot. This latter approach is referred to as Frequency Domain Analysis (FDA).

Scanning interferometry can be used to measure surface topography and/or other characteristics of objects having complex surface structures, such as thin film(s), discrete structures of dissimilar materials, or discrete structures that are underresolved by the optical resolution of an interference microscope. Such measurements are relevant to the characterisation of fiat panel display components, semiconductor wafer metrology, and in-situ thin film and dissimilar materials analysis. See, e.g., U.S. Patent Publication No. US-2004-0189999-A1 by Peter de Groot et al. entitled "Profiling Complex Surface Structures Using Scanning Interferometry" and published on Sep. 30, 2004, the contents of which are incorporated herein by reference, and U.S. Patent Publication No. US-2004-0085544-A1 by Peter de Groot entitled "Interferometry Method for Ellipsometry, Reflectometry, and Scatterometry Measurements, Including Characterization of Thin Film Structures" and published on May 6, 2004, the contents of which are incorporated herein by reference.

Other techniques for optically determining information about an object include ellipsometry and reflectometry. Ellipsometry determines complex reflectivity of a surface when illuminated at an oblique angle, e.g. 60°, sometimes with a variable angle or with multiple wavelengths. To achieve greater resolution than is readily achievable in a conventional ellipsometer, microellipsometers measure phase and/or intensity distributions in the back focal plane of the objective, also known as the pupil plane, where the various illumination angles are mapped into field positions. Such devices are modernizations of traditional polarization microscopes or "conoscopes," linked historically to crystallography and mineralogy, which employs crossed polarizers and a Bertrand lens to analyze the pupil plane birefringent materials.

Conventional techniques used for thin film characterization (e.g., ellipsometry and reflectometry) rely on the fact that the complex reflectivity of an unknown optical interface depends both on its intrinsic characteristics (material properties and thickness of individual layers) and on three properties of the light that is used for measuring the reflectivity: wavelength, angle of incidence, and polarization state. In practice, characterization instruments record reflectivity fluctuations resulting from varying these parameters over known ranges. Optimization procedures such as least-squares fits are then used to get estimates for the unknown parameters by minimizing the difference between measured reflectivity data and a reflectivity function derived from a model of the optical structure.

SUMMARY

The inventors have realized that an interferometry system capable of operating in multiple modes (e.g. profiling and ellipsometry modes), can provide a wealth of information which can be used in a complementary manner to provide accurate information about a test object.

For example, the inventors have realized that, for an interferometry system using a lens to image the exit pupil of an interferometer (or "back focal plane" or "Fourier plane"), a simple measurement scheme can characterize the system by determining, for example, attributes of the light source, illuminating and imaging optics, and interferometer cavity. Furthermore, these characteristics can be determined over a wide range of wavelengths, polarizations and angles of incidence. The attributes of the system can be determined from Interferometric measurement data alone, without requiring any direct inspection of the light source, optics, cavity, or any other of the many (often very sensitive) components of the interferometry system.

The measured interferometry system attributes provide a useful guide for use in assembly and quality control, and for comparing the system to other systems. Further, information can be used to improve the accuracy of measurements. For, example these attributes can be used to accurately modeling the interference signals that the system would measure for a given test surface structure. Such models are important for use in a number of Interferometric measurement and analysis schemes, especially those aimed towards accurately measuring complicated surfaces (e.g. those with including regions of disparate material properties, the film structures, and other surface features). We now summarize various aspects and features of the invention.

In one aspect, a method is disclosed, including: directing test light to a first calibration surface over a range of illumination angles and combining the test light emerging back from the first calibration surface with reference light to form an interference pattern, where the test light from the first calibration surface and die reference light are derived from a common source; directing at least a portion of the combined light from the first calibration surface to a multi-element detector so that different elements of the detector correspond to different illumination angles of the first calibration surface by test light; directing test light to a second calibration surface different from the first calibration surface over a range of illumination angles and combining the test light emerging back from the second calibration surface with reference light to form an interference pattern, where the test light from the second calibration surface and the reference light are derived from the common source; directing at least a portion of the combined light from the second calibration surface to the multi-element detector so that different elements of the detector correspond to different illumination angles of the second calibration surface by the test light.

Information is determined about an interferometry system based on interference signals measured by the different elements of the detector for the test light emerging from the first and second calibration surfaces and other information about the first and second calibration surfaces.

The information about the interferometry system includes information corresponding to at least one of: a spectral distribution of the common source, a relative attenuation of a polarization state perpendicular to the plane of incidence compared to a polarization state parallel to the plane of incidence, a variation of the spectral distribution of the illumination across a pupil plane of the interferometry system, a variation of the mean intensity of the illumination across a pupil plane of the interferometry system, a variation of the phase of the illumination across a pupil plane of the interferometry system, and a variation of the spectral intensity of the illumination across a pupil plane of the interferometry system.

The method can include a number of features, separately or in conjunction. For example. In some embodiments, the other information about the first and second calibration surfaces includes information about the reflectivity of the first and second calibration surfaces.

In some embodiments the first calibration surface includes; bulk silicon, an oxide layer on silicon, a dielectric layer on a substrate, an opaque metal layers on a substrate, a solid surface of a metal, a solid surface of a dielectric material.

In some embodiments, the method includes: comparing the information about the interferometry system to a standard calibration from the interferometry system; and modifying the interferometry system based on the comparison.

In some embodiments, the method includes: comparing the information about the interferometry system to information about a second interferometry system, and modifying one or both of the interferometry systems based on the comparison. In some embodiments, the method includes: generating multiple model scanning interferometry signals based on the information about the interferometer and information, about multiple models of a test object, where the multiple models of the test object are parametrized by a series of characteristics of the test object.

In some embodiments, the method includes: comparing information derivable from a scanning interferometry signal acquired by the interferometry system for a first surface location on a test object to information derivable from the multiple model scanning interferometry signals.

In some embodiments, the method includes: determining an accurate characteristic for the test object based on the comparison.

In some embodiments, the accurate characteristic is a surface height for the first surface location and/or a film thickness for the first surface location.

In some embodiments, the determining of the accurate characteristic includes determining which model of the test object corresponds to an accurate one of the characteristic for the test object based on the comparison, and using the model of the test object corresponding to the accurate characteristic to calculate information about the test object.

In some embodiments, the method includes comparing information derivable from the scanning interferometry signal for additional surface locations to the information derivable from the multiple model scanning interferometry signals.

In some embodiments, the method includes using a search engine to compare the information derivable from the scanning interferometry signal acquired by the interferometry system to the information derivable from the multiple model scanning interferometry signals.

In some embodiments, the comparing includes calculating one or more merit functions indicative of a similarity between the information derivable from the scanning interferometry signal and the information corresponding to each of the models.

In some embodiments, the method includes using the interferometry system to measure a test surface of a test object in a mode of operation that interferometrically profiles a topography of the test surface; and providing a corrected profile based on the information about the interferometry system.

In some embodiments, the test surface is a top surface of the test object or a buried surface of the test object.

In some embodiments, the method includes determining information about one or more areas on the test surface. The corrected profile is also based on the information about the one or more areas on the test surface.

In another aspect, a method is disclosed which includes, for each of multiple areas of a test surface on a test object having different reflectivities, using an interferometry system to measure each area in a first mode of operation that measures information about the reflectivity of the area over a range of angles and wavelengths; using the same interferometry system to measure the test surface in a second mode of operation that interferometrically profiles a topography of the test surface over a range including at least some of the multiple areas; and correcting the profile based on the information about the reflectivity of the multiple areas to reduce errors.

In some embodiments, the test surface is a top surface of the test object or a buried surface of the test object.

In some embodiments, the profile is a thickness profile.

In some embodiments, the correcting includes, for each area: determining a height offset based on the information about the reflectivity of the area; and adding the offset to the corresponding portion of the profile.

In some embodiments, the method includes using the same interferometry system to measure information about the reflectivity of two or more reference surfaces over a range of angles and wavelengths; using information about the reflectivity of the two or more reference surfaces to determine information about the interferometry system. The correcting of the profile is further based on the information about the interferometry system In some embodiments, the method includes determining additional information about the interferometer system based on the information about the reflectivity of the area over a range of angles and wavelengths. The correcting of the profile is further based on the information about the interferometry system.

In some embodiments, the method includes outputting the corrected profile. In some embodiments, the outputting of the corrected profile includes outputting to one of: a user, a display, electronic storage, an electronic controller, and electronic controller configured to operate one or more devices based on information related to the profile, printed media, and electronic storage media. In some embodiments outputting includes outputting for use in semiconductor metrology measurements.

In another aspect an interferometry system is disclosed including: a light source, a multi-element detector, an interferometer and an electronic processor. The interferometer is configured to:

direct test light to a first calibration surface over a range of illumination angles and combine the test light emerging back from the first calibration surface with reference light to form an interference pattern, where the test light from the first calibration surface and the reference light are derived from a common light source;

direct at least a portion of the combined light from the first calibration surface to the multi-element detector so that different elements of the detector correspond to different illumination angles of the first calibration surface by test light;

direct test light to a second calibration surface different from the first calibration surface over a range of illumination angles and combine the test light emerging back from the second calibration surface with reference light to form an interference pattern, where the test light from the second calibration surface and the reference light are derived from the light source; and direct at least a portion of the combined light from the second calibration surface to the multi-element detector so that different elements of the detector correspond to different illumination angles of the second calibration surface by the lest light.

The electronic processor is configured to:

determine information about the interferometry system based on interference signals measured by the different elements of the defector for the test light emerging from the first and second calibration surfaces and other information about the first and second calibration surfaces The information about the interferometry system includes information corresponding to at least one of: a spectral distribution of the common source, a variation of the spectral distribution of the illumination across a pupil plane of the interferometry system, a variation of the mean intensity of the illumination across a pupil plane of the interferometry system, a variation of the phase of the illumination across a pupil plane of the interferometry system, and a variation of the spectral intensity of the illumination across a pupil plane of the interferometry system.

In another aspect, an apparatus is disclosed including an interferometer system. The interferometer system is configured to operate in a first mode to, for each of multiple areas of a test surface on a test object having different reflectivities, measure information about the reflectivity of the area over a range of angles and wavelengths, operate in a second mode to interferometrically profile a topography of the test surface over a range including at least some of each of the multiple areas, and correct the profile based on information about the reflectivity of the multiple areas to reduce errors.

It is to be understood that any of the features described above may be include, alone or in combination, in various embodiments of the methods, apparatus and system, described above.

A pupil plane of an interferometry system is to be understood as the plane of an exit pupil of an interferometer, referred to by some as the "back focal plane" or "Fourier plane."

As used herein, "light" is not limited to electromagnetic radiation in the visible spectral region, but rather refers generally to electromagnetic radiation in any of the ultraviolet, visible, near infrared, and infrared spectral regions.

Unless otherwise defined, all technical and scientific terms used herein have the same meaning as commonly understood by one of ordinary skill in the art to which this invention belongs, in case of conflict with any document incorporated by reference, the present disclosure controls.

Other features, objects, and advantages of the invention will be apparent from the following detailed description.

DETAILED DESCRIPTION

Figure 1:
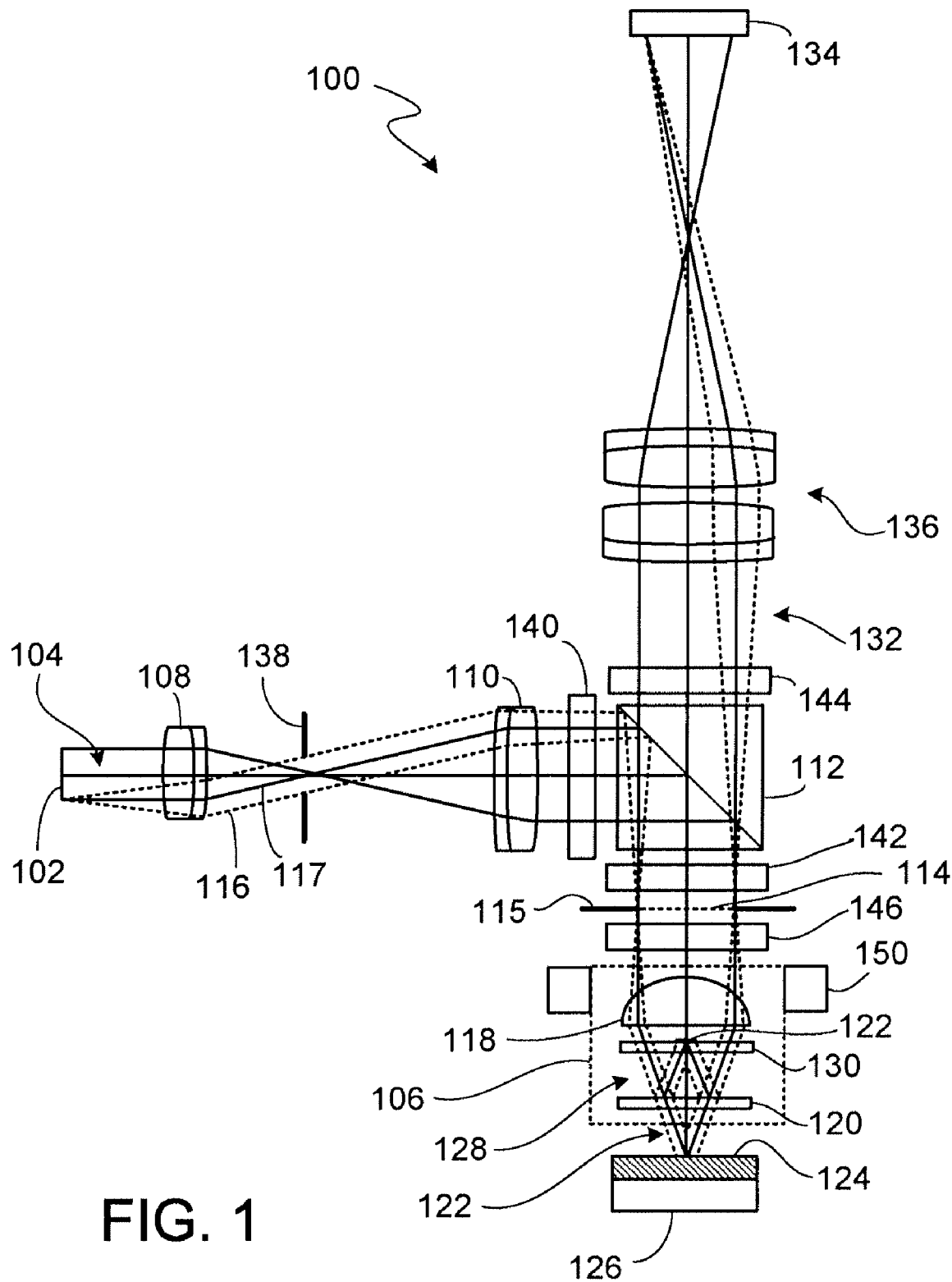
FIG. 1 is a schematic diagram of interferometry system 100 configured to operate in an ellipsometry mode.

Embodiments disclosed herein include an interferometry system and techniques for rapidly collecting a large number of reflectivity data points of an object over a wide range for all three optical characteristics of the interferometer probe beam (i.e., wavelength, angle of incidence, and polarization state) for a selected region of a test surface. This data is typically obtained by imaging the pupil plane of the interferometers, as described below.

Furthermore, the system can switch from the above described ellipsometry mode of operation to a profiling mode to provide laterally resolved information about the test surface. Moreover, information determined in the ellipsometry mode can be used to improve the accuracy of the information obtained in the profiling mode. For example, the ellipsometry mode can provide information about the material properties of the test object having the test surface to create more accurate topography maps of the various optical interfaces, the top surface (air interface), for example, being of particular interest. This multi-mode operation is described in more detail in U.S. patent application Ser. No. 11/335,873, entitled "INTERFEROMETER FOR DETERMINING CHARACTERISTICS OF AN OBJECT SURFACE," and filed Jan. 19, 2006, U.S. patent application Ser. No. 11/335,871, entitled "INTERFEROMETER WITH MULTIPLE MODES OF OPERATION FOR DETERMINING CHARACTERISTICS OF AN OBJECT SURFACE," and filed Jan. 19, 2006, and U.S. patent application Ser. No. 11/334,949, entitled "INTERFEROMETER FOR DETERMINING CHARACTERISTICS OF AN OBJECT SURFACE, INCLUDING PROCESSING AND CALIBRATION," and filed Jan. 19, 2006, and U.S. Provisional Patent Application Ser. No. 60/645,448, entitled "INTERFEROMETER FOR DETERMINING CHARACTERISTICS OF AN OBJECT SURFACE," and filed Jan. 20, 2005, each of which is in incorporated herein by reference.

Furthermore, techniques are disclosed for fully characterizing optical properties of the Interferometer and its light source by performing interferometric measurements of known surfaces in the pupil imaging mode. For instance, as described below, one can determine one or more of:

- the normalized spectral distribution of the light source, including its variations across the interferometer pupil.
- the variation of the source mean intensity or spectral intensity across the interferometer pupil.
- the amount of attenuation of polarization states that are perpendicular to the plane of incidence (S-polarization) compared to polarization states that are parallel to the plane of incidence (P-polarization) as they propagate through the entire optical system (from source to detector), as a function of wavelength and angle of incidence at the object surface.
- systematic offsets of the interference phase as a function of wavelength, angle of incidence and polarisation state (such effects can result for example from material thickness differences on the test and reference legs of the interferometer cavity, from the properties of beam splitter coatings, from wavefront distortions due to the beam splitter plate departure from flatness, etc).
- the range of illumination angles of incidence created by the optics at the object surface (possibly as a function of wavelength).
- the wavefront aberrations of the optical system, and their variation with wavelength (for instance by comparing the measured distribution of wavefront slopes to that expected, from the Abbé sine condition).

In some embodiments, these properties provide diagnostic information for the assembly of the interferometry system. They also provide quantitative information that can be used to create a matched set of instruments having similar characteristics, thereby allowing consistent measurements across multiple interferometers. This is a benefit for, e.g., production line testing involving multiple instruments.

In some embodiments, these properties are used as critical inputs for various models of the measurement process. The models produce synthetic interference signals that can be used for example, for library-based signal matching in the context of surface characterization (see e.g., U.S. Pat. No. 7,106,454, entitled PROFILING COMPLEX SURFACE STRUCTURES USING SCANNING INTERFEROMETRY, and filed, Mar. 8, 2004, the contents of which are incorporated herein by reference). The synthetic signals can also be analyzed in the same way as experimental signal to determine height offsets resulting from the surface optical properties. Examples are disclosed in the following sections.

Exemplary Apparatus

FIG. 1 is a schematic diagram of an interferometry system 100. A spatially extended source 102 directs input light 104 to an interference objective 106 via relay optics 108 and 110 and beam splitter 112. The relay optics 108 and 110 image input light 104 from spatially extended source 102 to an aperture stop 115 and corresponding pupil plane 114 of the interference objective 106 (as shown by the dotted marginal rays 116 and solid chief rays 117).

In the embodiment of the FIG. 1, interference objective 106 is of the Mirau-type, including an objective lens 118, beam splitter 120, and reference surface 122. Beam splitter 120 separates input light 104 into test light 122, which is directed to a test surface 124 of a test object 126, and reference light 128, which reflects from reference surface 122. Objective lens 118 focuses the test and reference light to the test and reference surfaces, respectively. The reference optic 130 supporting reference surface 122 is coated to be reflective only for the focused reference light, so that the majority of the input light passes through the reference optic before being split by beam splitter 120.

After reflecting from the test and reference surfaces, the test and reference light are recombined by beam splitter 120 to form combined light 132, which is transmitted by beam splitter 112 and relay lens 136 to form an optical interference pattern on an electronic detector 134 (for example, a multi-element CCD or CMOS detector). The intensity profile of the optical interference pattern across the detector is measured by different elements of the detector and stored in an electronic processor (not shown) for analysis. Unlike a conventional profiling interferometer in which the test surface is imaged onto the detector, in the present embodiment, relay lens 136 (e.g., a Bertrand lens) images different points on the pupil plane 114 to corresponding points on detector 134 (again as illustrating by dotted marginal rays 116 and solid chief rays 117).

Because each source point illuminating pupil plane 114 creates a plane wave front for test light 122 illuminating test surface 124, the radial location of the source point in pupil plane 114 defines the angle of incidence of this illumination bundle with respect to the object normal. Thus, all source points located at a givers distance from the optical axis correspond to a fixed angle of incidence, by which objective lens 118 focuses test light 122 to test surface 124. A field stop 138 positioned between relay optic 108 and 110 defines the area of test surface 124 illuminated by test light 122. After reflection from the lest and reference surfaces, combined light 132 forms a secondary image of the source at pupil plane 114 of the objective lens. Because the combined light on the pupil plane is then re-imaged by relay lens 136 onto detector 134, the different elements of the detector 134 correspond to the different illumination angles of test light 122 on test surface 124.

Polarization elements 140, 142, 144, and 146 define the polarization state of the test and reference light being directed to the respective test and reference surfaces, and that of the combined light being directed to the detector. Depending on the embodiment, each polarization element can be a polarizer (e.g., a linear polarizer), a retardation plate (e.g., a half or quarter wave plate), or a similar optic that affects the polarization state of an incident beam. Furthermore, in some embodiments, one or more of the polarization elements can be absent. Moreover, depending on the embodiment, beam splitter 112 can be polarizing beam splitter or a non-polarizing beam splitter. Details of various embodiments for these polarization elements are described further below. In general, because of the presence of polarization elements 140, 142 and/or 146, the state of polarization of test light 122 at test surface 124 can be a function of the azirauthal position of the light in pupil plane 114.

In the presently described embodiment, source 102 provides illumination over a broad hand of wavelengths (e.g., an emission spectrum having a full-width, half-maximum of more than 50 nm, or preferably, even more than 100 nm). For example, source 102 can be a white light emitting diode (LED), a filament of a halogen bulb, an arc lamp such as a Xenon arc lamp or a so-called supercontinuum source that uses non-linear effects in optical materials to generate very broad source spectra (>200 nm). The broad band of wavelengths corresponds to a limited coherence length. As in conventional scanning interferometer, a translation stage 150 adjusts the relative optic path length between the test and reference light to produce an optical interference signal at each of the detector elements. For example, in the embodiment of the FIG. 1, translation stage 150 is a piezoelectric transducer coupled to interference objective 106 to adjust the distance between the test surface and the interference objective, and thereby vary the relative optical path length between the test and reference light at the detector.

Figure 2:
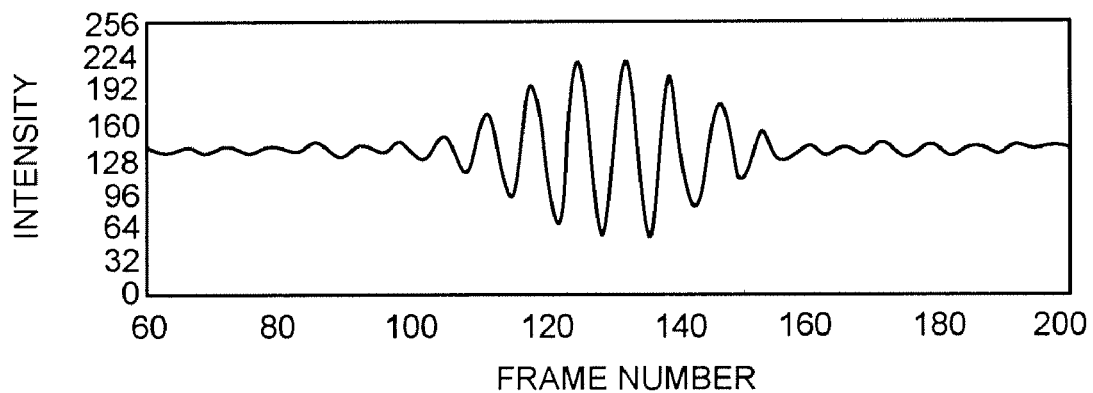
FIG. 2 is a graph showing an example of an interferometry signal measured a detector element when the optical path length difference ("OPD") between the test and reference light in interferometry system 100 is varied, where the OPD is expressed by camera frame number.

FIG. 2 shows an exemplary interference signal measured by one of the detector elements as the translation stage varies the relative optical path length between the test and reference light. The interference signal is modulated by a contrast envelope corresponding to the coherence length of the source. The reference surface is positioned in the interferometer so that a zero optical path length difference between the test and reference light corresponds to a position of the test surface that is in focus with respect to objective lens 118. Thus, maximum contrast is generally observed when the test surface is in this in-focus position relative to the interference objective. A measurement is performed by scanning the translation stage over a range larger than the coherence length so that the contrast envelope is captured in a sequence of intensity patterns measured at the detector.

The interference signal measured at each detector element is analyzed by the electronic processor, which is electronically coupled to both detector 134 and translation stage 150. In the presently described embodiment, the electronic processor transforms the interference signal into the frequency domain, for example, by using a Fourier transform, to extract the phase and amplitude information for the different wavelength components of the light source. Preferably, the source spectrum is broad so that many independent spectral components can be calculated with this procedure. As will be described in greater detail below, the amplitude and phase data relate directly to the complex reflectivity of the test surface, which can be analyzed to determine information about the test object. Generally, the electronic processor uses information from a separate calibration to correct the measurement for the reflectivity of the reference mirror and other optical characteristics of the interferometer. Because of the arrangement of interferometry system 100, each defector element of electronic detector 134 provides reflectivity measurements at a multiplicity of wavelengths produced by source 102, for a specific angle of incidence and polarization state (according to the orientations of polarization elements 140, 142, 144 and/or 146). The collection of detector elements thus covers a range of angles of incidence, polarization states and wavelengths, which maximizes the ability of the instrument to properly characterize unknown optical structures.

A number of calibration procedures can be used to derive the complex reflectivity of the test surface from the measured interference signals. For example, a calibration measurement can be made with a mirror made of known bulk material (opaque or transparent) as the test object, and a spectral filter can be used to isolate a selected wavelength from the source. The interference signals measured on the detector can then be processed to determine the angle of incidence corresponding to each detector element and the speed of the scanning stage used for data acquisition. The latter information is useful to properly match the interference signal spectral components to their respective wavelengths. Additional measurements using objects of known optical properties can also be used to derive the properties of the interferometer and imaging system on a pixel-by-pixel basis. For example, a calibration may include the steps of calculating the transmission of the system for each wavelength and at each detector position. Similarly, polarization effects such as phase offsets introduced between orthogonal states of polarization can also be measured for each detector element and for each wavelength if required. Specific details for certain embodiments of the calibration are described further below.

Figure 3:
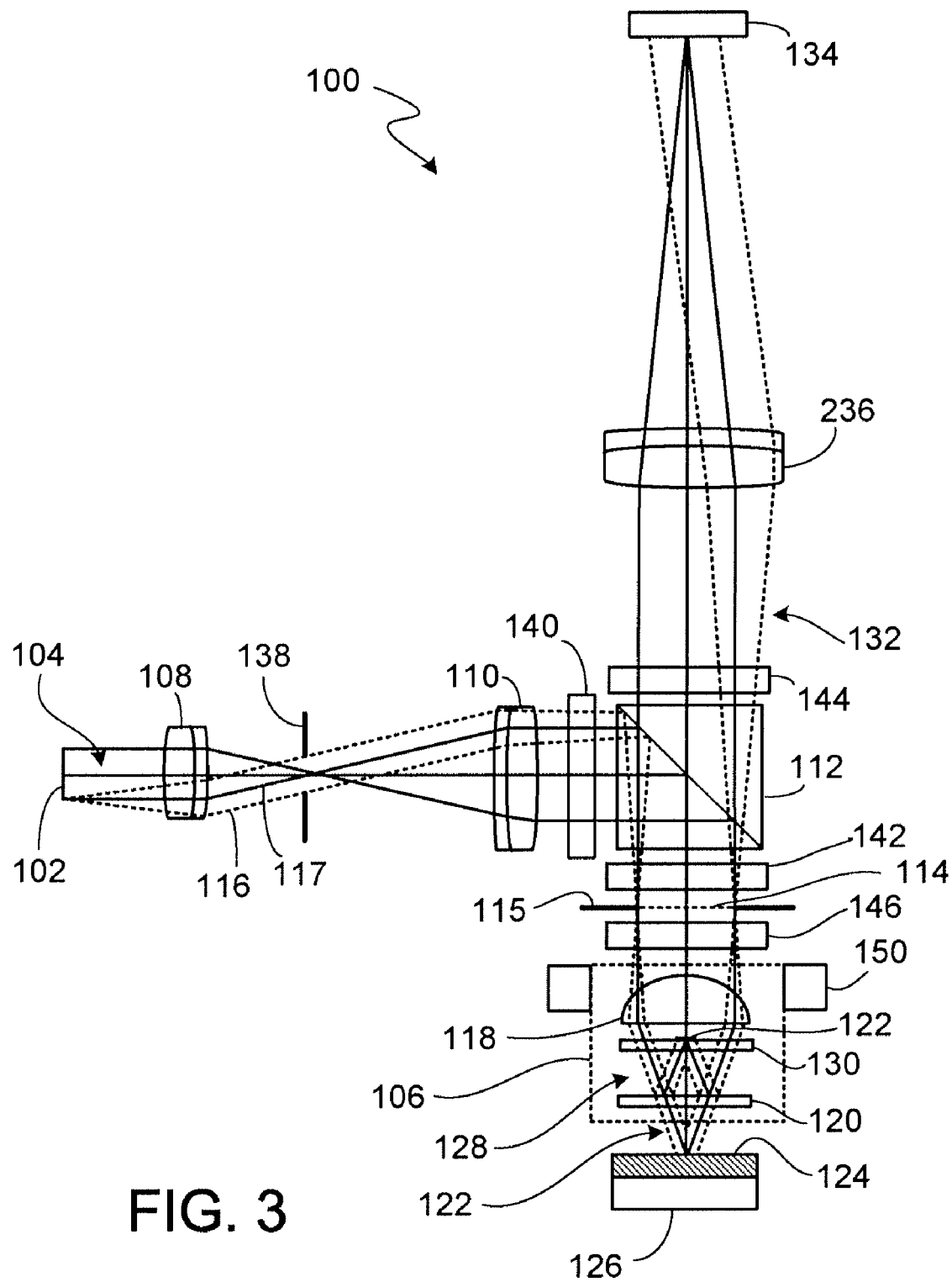
FIG. 3 is a schematic diagram of interferometry system 100 reconfigured to operate in a profiling mode.

To switch interferometry system 100 from an ellipsometry mode for a determining the complex reflectivity of the test surface, to a profiling mode for determining, for example, the topography of the test surface, it is sufficient to change the properties of the imaging system so that the image of the part comes in focus on the detector instead of the image of the source. As shown in FIG. 3, this can be accomplished, for example, by replacing the relay lens 136 by another lens 236 and keeping the detector position fixed. In this case, the input light from source 102 continues to be imaged to pupil plane 114, however, the points on 124 are imaged to corresponding points on detector 134 (as indicated by marginal rays 216 and chief rays 217 from source 102). As described in U.S. patent application Ser. No. 11/335,871, entitled "INTERFEROMETER WITH MULTIPLE MODES OF OPERATION FOR DETERMINING CHARACTERISTICS OF AN OBJECT SURFACE," and filed Jan. 19, 2006, the replacement of the lens can be accomplished mechanically, allow quick and efficient switching between operational modes.

For example, FIG. 1a shows a schematic diagram of how various components in Interferometry system 100 can be automated under the control of electronic processor 970, which, in the presently described embodiment, can include an analytical processor 972 for carrying out mathematical analyses, device controllers 974 for controlling various components in the interferometry system, a user interface 976 (e.g., a keyboard and display), and a storage medium 978 for storing calibration information, data files, a sample models, and/or automated protocols.

First the system can include a motorized turret 910 supporting multiple objectives 912 and configured to introduce a selected objective into the path of input light 104. One or more of the objectives can be interference objectives, with the different interference objectives providing different magnifications. Furthermore, in certain embodiments, one (or more) of the interference objectives can be especially configured for the ellipsometry mode of operation by having polarization element 146 (e.g., a linear polarizer) attached to it. The remaining interference objectives can be used in the profiling mode and, in certain embodiments, can omit polarization element 146 so as to increase light, efficiency (such as for the embodiment described above in which beam splitter 112 is a polarizing beam splitter and polarization element is 142 is a quarter wave plate). Moreover, one or more of the objectives can be a non-interferometric objective (i.e., one without a reference leg), each with a different magnification, so that system 100 can also operate in a conventional microscope mode for collecting optical images of the test surface (in which case the relay lens is set to image of test surface to the detector). Turret 910 is under the control of electronic processor 970, which selects the desired objective according to user input or some automated protocol.

Next, the system includes a motorized stage 920 (e.g., a tube lens holder) for supporting relay lenses 136 and 236 and selectively positioning one of them in the path of combined light 132 for selecting between the first mode (e.g., an ellipsometry or reflectometry mode) in which the pupil plane 114 is imaged to the detector and the second mode (e.g., profiling or microscope mode) in which the test surface is imaged to the detector. Motorized stage 920 is under the control of electronic processor 970, which selects the desired relay lens according to user input or some automated protocol. In other embodiments, in which a translation stage is moved to adjust the position of the detector to switch between the first and second modes, the translation is under control of electronic processor. Furthermore, in those embodiments with two detection channels, each detector is coupled to the electronic processor 970 for analysis.

Furthermore, the system can include motorized apertures 930 and 932 under control of electronic processor 970 to control the dimensions of field stop 138 and aperture stop 115, respectively. Again the motorized apertures are under the control of electronic processor 970, which selects the desired settings according to user input or some automated protocol.

Also, translation stage 150, which is used to vary the relative optical path length between the test and reference legs of the interferometer, is under the control electronic processor 970. As described above, the translation stage can be coupled to adjust the position of the interference objective relative to a mount 940 for supporting test object 126. Alternatively, in further embodiments, the translation stage can adjust the position of the interferometry system as a whole relative to the mount, or the translation stage can be coupled to the mount, so it is the mount that moves to vary the optical path length difference.

Furthermore, a lateral translation stage 950, also under the control of electronic processor 970, can be coupled to the mount 940 supporting the test object to translate laterally the region of the test surface under optical inspection. In certain embodiments, translation stage 950 can also orient mount 940 (e.g., provide tip and tilt) so as to align the test surface normal to the optical axis of the interference objective.

Finally, an object handling station 960, also under control of electronic processor 970, can be coupled to mount 940 to provide automated introduction and removal of test samples into system 100 for measurement. For example, automated wafer handling systems known in the art can be used for this purpose. Furthermore, if necessary, system 100 and object handling system can be housed under vacuum or clean room conditions to minimize contamination of the test objects.

The resulting system provides great flexibility for providing various measurement modalities and procedures. For example, the system can first be configured in the microscope mode with one or more selected magnifications to obtain optical images of the test, object for various lateral positions of the object. Such images can he analysed by a user or by electronic processor 970 (using machine vision techniques) to identify certain regions (e.g., specific structures or features, landmarks, fiducial markers, defects, etc.) in the object. Based on such identification, selected regions of the sample can then be studied in the ellipsometry mode to determine sample properties (e.g., refractive index, underlying film thickness(es), material identification, etc.).

Accordingly, the electronic processor causes stage 920 to switch the relay lens to the one configured for the ellipsometry mode and further causes turret 910 to introduce a suitable interference objective into the path of the input light. To improve the accuracy of the ellipsometry measurement, the electronic processor can reduce the size of the field stop via motorized aperture 930 to isolate a small laterally homogenous region of the object. After the ellipsometry characterization is complete, electronic processor 970 can switch the instrument to the profiling mode, selecting an interference objective with a suitable magnification and adjusting the size of field stop accordingly. As described above, the profiling mode captures interference signals that allow reconstructing the topography of, for example, one or more interfaces that constitute the object. Notably, as described in greater detail below, the knowledge of the optical characteristics of the various materials determined in the ellipsometry mode allows for correcting the calculated topography for thin film or dissimilar material effects that would otherwise distort the profile. See, for example, U.S. patent application Ser. No. 10/795,579 entitled "PROFILING COMPLEX SURFACE STRUCTURES USING SCANNING INTERFEROMETRY" and published as U.S. Patent Publication No. US-2004-0189999-A1, which was incorporated by reference above. If desired, the electronic processor can also adjust the aperture stop diameter via motorized aperture 932 to improve the measurement in any of the various modes.

When used in conjunction with automated object handling system 960, the measurement procedure can be repeated automatically for a series of samples. This could be useful for various process control schemes, such as for monitoring, testing, and/or optimizing one or more semiconductor processing steps.

Measurement Model

To demonstrate the analysis of the interference signals obtained by interferometry system 100, we consider an embodiment in which polarization elements 140 and 144 are linear polarizers, polarization elements 142 and 146 are absent, and beam splitter 112 is a non-polarizing beam splitter. The effect of the linear polarizer 140 is to create an identical linear polarization state at every point in pupil plane 114. As a result, the polarization of the light incident on test surface 124 is linear, but its orientation with respect to the plane of incidence is a function of the azimuthal location of the source point at the pupil plane. For example, the source points that belong to a pupil diameter that is parallel to the direction of the linear polarization in the pupil plane will generate illumination light that is linearly polarized within the plane of incidence at the test surface (this is called the P polarization state). Similarly, the source points that belong to a diameter that is perpendicular to the direction of the linear polarization in the pupil plane will generate illumination light that is linearly polarized perpendicularly to the plane of incidence (this is called the S polarization state). Source points that do not belong to these two diameters will create illumination light on the test surface that has a mix of S and P polarization states. This is relevant because the reflectivity coefficients for the test surface are different for S and P polarized light.

The two linear polarizers can have a number of relative orientations that will dictate the content of the interference signal detected by the detector. For example, if the polarizers are parallel then the measured interference signal will depend solely on S-polarized test light being incident on the test surface for one diameter of the pupil plane and depend solely on P-polarized test light being incident on the test surface for an orthogonal diameter of the pupil plane (and similarly, for the reference light incident on the reference surface). This is attractive because the difference between the magnitude and phase of S and P reflectivities is the basis for ellipsometry. If desired, therefore, simplified processing of the data can be restricted to these two diameters. On the other hand, using the data over the entire pupil plane requires taking into account the mix of the two polarization states, but provides more data points and thus increases the resolution of the measurement.

The following analysis applies to the arrangement with the two linear polarizers aligned parallel to one another. In this case, the amount of test light that is transmitted through the second linear polarizer (polarization element 144) to detector 134 can be expressed as:

$$E_{out} = \frac{1}{2}(\cos(\theta)^2 rp \cdot tp - \sin(\theta)^2 rs \cdot ts)E_{in} \quad (1)$$

where θ is the azimuth angle measured with respect to the direction of the polarizers, rp and rs are the complex, reflection coefficients of the object surface for P and S polarization states (known as the "Fresnol reflection coefficients"), tp and ts are the transmission coefficients for P and S polarization states for the round, trip through the interference objective 106 and the main beam splitter 112 and $E_{out}$ is the complex amplitude of the electric field. This model assumes that the optics are free from birefringence and that reflection off the object surface is also free from mechanisms that would mix the S and P polarizations states. For example, a uniaxial material with its axis along the local surface normal can he characterized in this context, however, a material having in-plane birefringence requires a different model.

In practice, the same model applies for the reference light that propagates along the reference leg of the interferometer, however, the reflection and transmission coefficients are a priori different:

$$E_{out}^r = \frac{1}{2}(\cos(\theta)^2 rp^r \cdot tp^r - \sin(\theta)^2 rs^r \cdot ts^r)E_{in} \quad (2)$$

The interference pattern that is measured at the detector for a given source wavelength λ and a given source point at the pupil plane consists of a modulating term that is proportional to the product $E_{out}E_{out}^r$:

$$\text{Intensity}(k,\alpha,z) = |E_{out}|^2 + |E_{out}^r|^2 + 2|E_{out}||E_{out}^r|\cos(2k\cos(\alpha)z + \phi(k,\alpha)) \quad (3)$$

where k=2π/λ, λ is the wavelength of the light, z is the vertical location of the test surface during a mechanical scan relative to a zero optical path length difference between the test and reference light, α is the angle of incidence of the light at the test surface (which depends on the source point location at the pupil) and φ is a phase difference between the test and reference electric fields. In practice, the signal measured at a given detector location is the sum of all such signals generated by the various wavelengths present in the source spectrum. As a result a Fourier transformation of the signal allows separating these contributions into complex spectral components corresponding to very narrow wavelength ranges. Note that in order to assign a calculated spectral component to a specific source wavelength one should take into account, the correction factor cos(α), which shifts the location of these spectral components. This correction factor involves knowing the angle of incidence of light at each pixel of the detector. A calibration of the optical system can be used for this task and is discussed further below.

Figure 4:
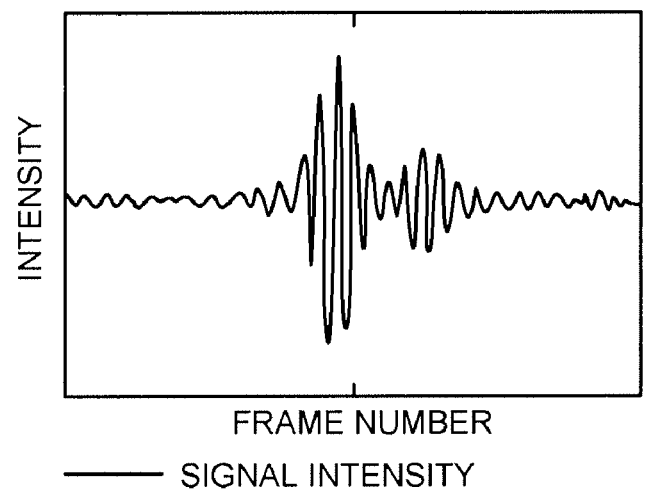
FIG. 4 shows plots of a data collected by a detector element for a test object having 1-micron thick silicon dioxide film on a silicon substrate. The left plot shows interferometry signal measured by the detector element as a function of frame number during the OPD scan. The right plot shows the Fourier transform of the interferometry signal with respect to wavenumber, with spectral magnitude being shown by solid trace and spectral phase being shown by the dotted trace.
Figure 4:
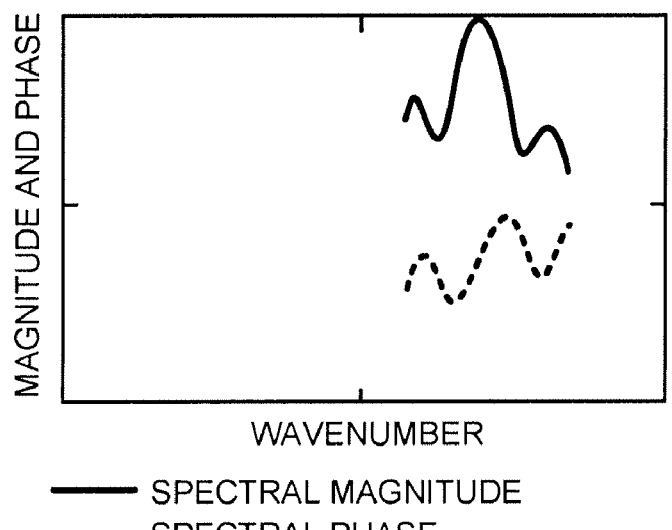

FIG. 4 (upper plot) shows a representative interference signal measured by a given detector element of detector 134 (corresponding to a given location in the pupil plane) when measuring a 1003-nm thick silicon dioxide film on silicon. FIG. 4 (lower plot) shows the result of Fourier transforming the interference signal to yield the spectral magnitude and phase as function of wavelength (or the corresponding wavenumber k). The variation in the spectral magnitude and phase is a result of the variation of the Fresnel reflection coefficient as a function of the wavelength (or wavenumber).

In certain embodiments, the frequency transform processing is applied to a region of interest within the image of the pupil plane on the detector. For example, the region of interest can be an annulus, which defines a given range of angles of incidence at the test surface. The azimuthal location of a pixel (i.e., one of the detector elements) within this annulus defines the mix of S and P polarization that illuminates the test surface and the radial distance of the pixel to the optical axis defines the angle of incidence. Furthermore, it can be useful to extract (possibly using interpolation) the spectral components as described above over multiple circles within the region of interest. These components calculated over one such circle can be written in the form:

$$Z_{\alpha\lambda\theta} = L_\lambda I_{\alpha\lambda\theta} \exp(i\varphi_{\alpha\lambda h})(\cos(\theta)^2 \rho_{\alpha\lambda} - \sin(\theta)^2 \tau_{\alpha\lambda}) \quad (4)$$

with $$\rho_{\alpha\lambda} = \frac{rp_{\alpha\lambda}}{rs_{\alpha\lambda}} \text{ and } \tau_{\alpha\lambda} = \frac{ts_{\alpha\lambda}}{tp_{\alpha\lambda}}$$

where the subscripts denote a functional dependence, α is the angle of incidence corresponding to the radius of the circle at the pupil plane, λ is the wavelength of light, θ is the azimuthal angle measured with respect to the linear polarizers, h is a height offset of the object surface, L is a real scaling factor related to the source intensity or signal strength and I is a complex function that represents the variations of the light intensity across the source as well as phase and amplitude variations occurring in the optics.

Interferometry System Characterization

In certain embodiments, a first step of the system calibration includes calculating the angle of incidence of a beam bundle at the test surface based on the Location of the source point in the pupil plane. In other words, we want to assign an angle of incidence α to each pixel in the detector corresponding to the image of the pupil plane. This can be accomplished, for example, by performing a measurement with a narrow-band filter so that the light detected by the defector is essentially monochromatic and has a known, wavelength. In this case, Eq. (3) shows that the frequency of the interference signal is proportional to the source wavelength and the angle of incidence through the relationship k cos α. The signal frequency can he calculated by a Fourier transform of the signal and the angle of incidence can be derived from the knowledge of the scan rate of the translation stage and the source wavelength.

Furthermore, to the extent the scan rate of the translation stage is initially unknown, it can be determined by locating the pixel on the detector whose interference signal, has the largest frequency. According to the frequency's dependence on the relationship k cos α, this pixel corresponds to normal incidence (i.e., α=0), and so the stage speed can be extracted directly from the measured frequency and knowledge of the source wavelength.

Note that a priori information on the way the microscope objective maps angles in object space onto pupil positions can also be used to improve the quality of this calibration. For example, a typical objective is corrected for coma (a geometric aberration), which implies that the ray mapping at the pupil should nominally obey the so-called "Abbé sine condition." This condition means that the radial distance of a source point from the optical axis at the pupil is directly proportional to the sine of the angle of incidence in object space. One can thus calculate the angle of incidence for each pixel and then fit a global function. derived from the sine condition to provide an analytical function snapping pupil position to angle of incidence.

The deviation of the angle of incidence map from an ideal angular distribution across the pupil provides information on wavefront aberrations. This can be used for instance to optimize the internal compensation for spherical aberration for certain types of interferometers. Repeated measurements at different wavelengths provide further information and a means of balancing aberrations according to the source spectral distribution.

Note also that the angle of incidence maps also directly measure the useful range of illumination directions allowed by the various physical stops present in the optical system. This can be different from the nominal numerical aperture expected for a given optical system. The actual range of angles is critical for accurate modeling of the measurement system.

In certain embodiments, the procedure outlined above can be repeated for different nominal source wavelengths so that chromatic variations of the angular mapping are taken into account. A by-product of the fitting procedure is the pixel position of the optical axis at the pupil. That information is also recorded as a function of wavelength and can be used later on to apply corrections to angle of incidence calculations.

For certain embodiments, the calibration involves calculating the value of the various system parameters that relate the observable Z expressed in Eq. (4) to the ellipsometric ratio.

For example, this can be accomplished by measuring two samples that have known optical properties, for example calibration wafers typically used with ellipsomeeters. For each angle of incidence and wavelength of interest the electronic processor determines the spectral components Z as a function of azimuth angle θ as in Eq. (4) for both samples. The ratio of these components is then calculated, yielding the complex ratio z as a function of θ.

$$z_{\alpha\lambda\theta} = \frac{Z_{\alpha\lambda\theta}^a}{Z_{\alpha\lambda\theta}^b} = \frac{L_\lambda^a}{L_\lambda^b} \exp(i\varphi_{\alpha\lambda ha} - i\varphi_{\alpha\lambda hb}) \frac{\cos(\theta)^2 \rho_{\alpha\lambda}^a - \sin(\theta)^2 \tau_{\alpha\lambda}}{\cos(\theta)^2 \rho_{\alpha\lambda}^b - \sin(\theta)^2 \tau_{\alpha\lambda}} \quad (5)$$

or $$z_{\alpha\lambda\theta} = zs_{\alpha\lambda} \frac{\cos(\theta)^2 \rho_{\alpha\lambda}^a - \sin(\theta)^2 \tau_{\alpha\lambda}}{\cos(\theta)^2 \rho_{\alpha\lambda}^b - \sin(\theta)^2 \tau_{\alpha\lambda}}$$

where $zs_{\alpha\lambda}$ and $\tau_{\alpha\lambda}$ are unknown complex numbers and the a or b superscripts identify one or the other calibration sample. $\rho_{\alpha\lambda}^a$ and $\rho_{\alpha\lambda}^b$ are calculated using the ratio of the reflection coefficients for the two materials. These coefficients are themselves calculated using the known material properties and known film thicknesses (if present) of the calibration samples. The electronic processor can then use a solver, for example a least-squares solver based on the Levenberg-Marquardt algorithm, to find the value of the two unknown parameters that minimize the difference between the quantities calculated on both sides of Equation (5). The process is repeated for other angles of incidence and wavelengths. In various embodiments, the measurement of the two samples may occur concurrently or sequentially. Note that in some embodiments, the calibration surfaces may be included in a single object, which may further include other surfaces.

The calibration surfaces are a preferably smooth, having limited lateral variations of their optical properties within the size of the measurement spot of the interferometer. The optical properties (e.g., material properties and thickness of material layers) should be known with a low uncertainty. Additionally, the two surfaces should be chosen such that their complex reflectivity coefficients differ over the range of wavelength and angles of incidence of interest. Exemplary Surfaces include dielectric films (for example certified silicon dioxide samples on silicon substrates), opaque metal layers on substrates, solid surface of metals or dielectric materials, etc. Important factors in choosing a suitable calibration surface include knowledge of the optical properties of the sample, the stability of these properties as a function of time, exposure to atmosphere, etc.

In certain embodiments, another step of the calculation involves establishing the exact angular orientation of the polarizers with respect to the coordinate system of the pupil as seen by the detector. This can be done, for example, by observing that Equation (5) is periodic in θ with a period π. It follows that the phase of the even components of the Fourier transform of the ratio z is a direct measurement of the angular offset of the polarizer. Accordingly, this calculation can be performed before determining $zs_{\alpha\lambda}$ and $\tau_{\alpha\lambda}$.

In a further step, the maps $zs_{\alpha\lambda}$ and $\tau_{\alpha\lambda}$ are filtered and/or fitted to analytical functions. It is then possible to reprocess the spectral components obtained for each sample and derive another calibration parameter, the function J:

$$J_{\alpha\lambda\theta} = \frac{Z_{\alpha\lambda\theta}^a}{\cos(\theta)^2 \rho_{\alpha\lambda}^a - \sin(\theta)^2 \tau_{\alpha\lambda}} = L_\lambda^a I_{\alpha\lambda\theta} \exp(i\varphi_{\alpha\lambda ha}) \quad (6)$$

or $$J_{\alpha\lambda\theta} = \frac{Z_{\alpha\lambda\theta}^b}{\cos(\theta)^2 \rho_{\alpha\lambda}^b - \sin(\theta)^2 \tau_{\alpha\lambda}} zs_{\alpha\lambda} = L_\lambda^a I_{\alpha\lambda\theta} \exp(i\varphi_{\alpha\lambda ha})$$

In practice, the two expressions for J shown in Equation (6) can be averaged. The calculated values of J as a function of angle of incidence, wavelength and azimuth angle are then stored by the electronic processor in a calibration file along with the definition of the function $\tau_{\alpha\lambda}$.

Note that the procedure outlined above could be extended to more than two samples in order to benefit from redundancy in the calculation.

The calibration parameter $J(\alpha,\lambda,\theta)$ and the factor $\tau(\alpha,\lambda)$ provide a wealth of information which can be used, along with the techniques described above, to characterize the properties of and interferometry system. The factor $\tau(\alpha, \lambda)$ provides a measure of the attenuation of S-polarized light compared to P-polarized light as a function of wavelength and angle of incidence at the object. As described below, the calibration parameter $J(\alpha, \lambda, \theta)$ provides a number of other useful pieces of information.

For example, the magnitude of $J(\alpha, \lambda, \theta)$ measures the spectral distribution of the light source and its variation, over the pupil. Furthermore, the phase of $J(\alpha, \lambda, \theta)$ provides information about systematic wavelength and angle of incidence dependent phase offsets that result from differences in optical properties of the test and reference paths in the interferometer. In the following, we will describe how knowledge of the calibration parameter $J(\alpha, \lambda, \theta)$ and the depolarization factor $\tau(\alpha, \lambda)$ can be analyzed to characterize the properties of the interferometer. Information about these properties may then be used, for example, in quality control during assembly of the interferometry system and/or to provide useful inputs when modeling the signal of the interferometer in the ellipsometry and/or profiling mode. Note that, in various embodiments, it is often useful to fit analytical approximations to one or more of the above parameters, thereby allowing analytical manipulation in the calculations described below.

For specific optical configurations it is possible to decouple some of the parameter dependence further simplifying the modeling process. This happens for instance when the wavelength distribution measured by the detector is the same regardless of the location at the pupil. This implies that light intensity distribution at the pupil is independent of wavelength. The source spectrum is then calculated as:

$$V(\lambda) = \int\int |J(\alpha, \lambda, \theta)| d\alpha d\theta \quad (7)$$

Figure 5:
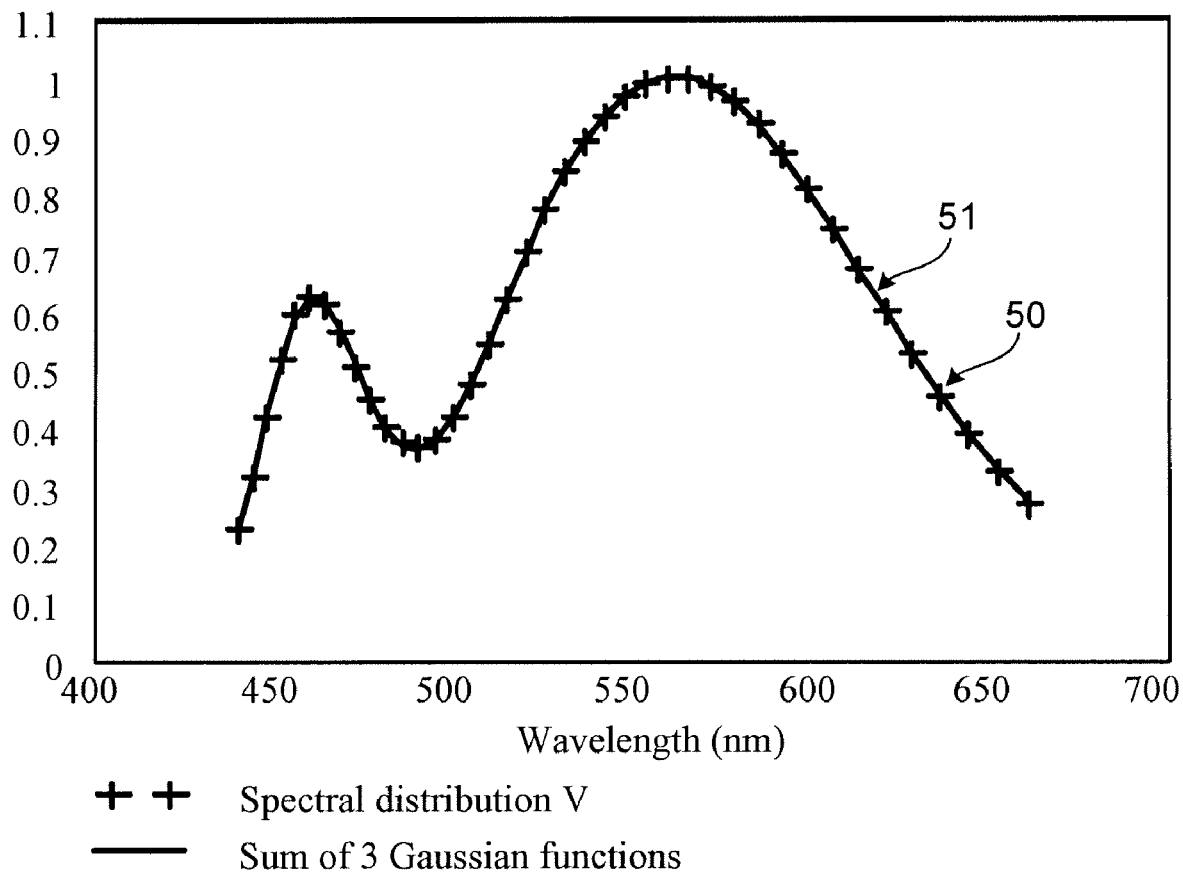
FIG. 5 shows a plot of a spectral distribution of an illumination source, along with an analytical approximation.

For example FIG. 5 shows an example spectrum 50 measured in this fashion ("+" markers). Also shown is an analytical approximation 51 defined as the sum of three Gaussian functions fit to the experimental data.

The intensity at the pupil is calculated from/at a specific wavelength $\lambda_u$:

$$D_L(\alpha, \theta) = |J(\alpha, \lambda_u, \theta)| \cos \alpha. \quad (8)$$

The cosine term accounts for a spectral scaling of the Fourier transform as described above. This distribution can be approximated by an analytical function by fitting the experimental data to a model function using, for example, a least-squares procedure. The model function is for instance a sum of standard polynomials or Zeroike polynomials, The phase distribution at the pupil is calculated by collecting the argument of the function J for each wavelength and angle of incidence:

$$A(\alpha, \lambda) = \frac{1}{2\pi} \int_0^{2\pi} \arg(J(\alpha, \lambda, \theta)) d\theta \quad (9)$$

One such data sequence (fixed $\alpha$ and $\lambda$) defines a "ring" of data. This calculation might require the extra step of unwrapping the phase of J as a function of $\theta$ for fixed values of a and $\lambda$. The reason, for this process step is that, in some embodiments, phase can usually only be calculated modulo $2\pi$. Consequently, it is possible to obtain sharp $2\pi$ phase jumps between successive phase values that are known to be samples of a continuous phase distribution, in this case the phase unwrapping procedure removes potential $2\pi$ phase jumps. For example, if $\Omega_i (i \in [1, N])$ represents a sequence of phase values, phase unwrapping may be accomplished by sequentially applying the following formula $$\Omega_{i+1} = \Omega_{i+1} - 2\pi \, \text{round}\left(\frac{\Omega_{i+1} - \Omega_i}{2\pi}\right) \quad (10)$$

where the round( ) function rounds a real number to the nearest integer number.

In some cases it is useful to preserve more than just the average value of the argument as shown in Eq.(9). This can, for example, be accomplished by collecting the first few Fourier coefficients of the different, previously acquired rings of data. One may then use analytical fit functions to describe the variation of the Fourier coefficients as a function of $\alpha$ and $\lambda$. In this case the function, describing the phase depends on three variables: $\tilde{A}(\alpha, \lambda, \theta)$. Note that in all eases:

$$A(\alpha, \lambda) = \frac{1}{2\pi} \int_0^{2\pi} \tilde{A}(\alpha, \lambda, \theta) d\theta \quad (11)$$

The optical system characterization described earlier provides the factor $\tau(\alpha, \lambda)$ when a linear polarizer is located at the objective pupil or when polarizers defining parallel polarization states are located both on the illumination and imaging sections of the optical system. In the case where the objective is used with unpolarized or circularly polarized light it is necessary to first, perform the linearly-polarized system characterization. Next, the measurement of a single reference object with unpolarized or circularly polarized light is sufficient to provide a second calibration parameter $J_c(\alpha, \lambda, \theta)$ that can be processed as described earlier.

In some optical configurations, the pupil intensity distribution takes a simplified form where azimuthal dependence is dropped:

$$D_c(\alpha) = \frac{1}{2\pi} \int_0^{2\pi} |J_c(\alpha, \lambda_u, \theta)| d\theta \quad (12)$$

Note however that the azimuthal dependence of the phase of $J_c(\alpha, \lambda, \theta)$ may have to be preserved in some cases, for instance modeled as a function $\tilde{A}(\alpha, \lambda, \theta)$.

Quality Control

It will be understood that the above described techniques provide quantitative information regarding a number of interferometry system characteristics. For example, analysis of parameter $J(\alpha, \lambda, \theta)$ can provide information about pupil illumination uniformity, the source spectrum measured at the detector, source spectrum variations across the pupil, wavefront quality in object space at different wavelengths, wavefront distortion due to the beam splitter present in the interferometer cavity, chromatic aberrations of the interference objective, and imbalance of transparent material thickness encountered on test and reference legs (the source of large variations of the argument of $J(\alpha, \lambda\theta)$. Additionally, techniques are described above which may be used to determine, for example, the effective numerical aperture of the objective, velocity of the scanning stage, attenuation due to optical coatings and optics materials of a radial polarization state compared to a tangential polarization state. Furthermore, birefringence properties of the objective may be determined by performing multiple measurements with varying illumination and imaging polarization states (for instance two adjustable linear polarizers on the illumination and Imaging legs).

Notably, all of the above described properties are determined based on pupil plane measurements alone, and do not require direct analysis of the individual elements of the interferometer. For example, the illumination, source spectrum may be determined directly from interferometric data, without examining the source directly. Thus the interferometer can be characterized quickly and efficiently.

Figure 7:
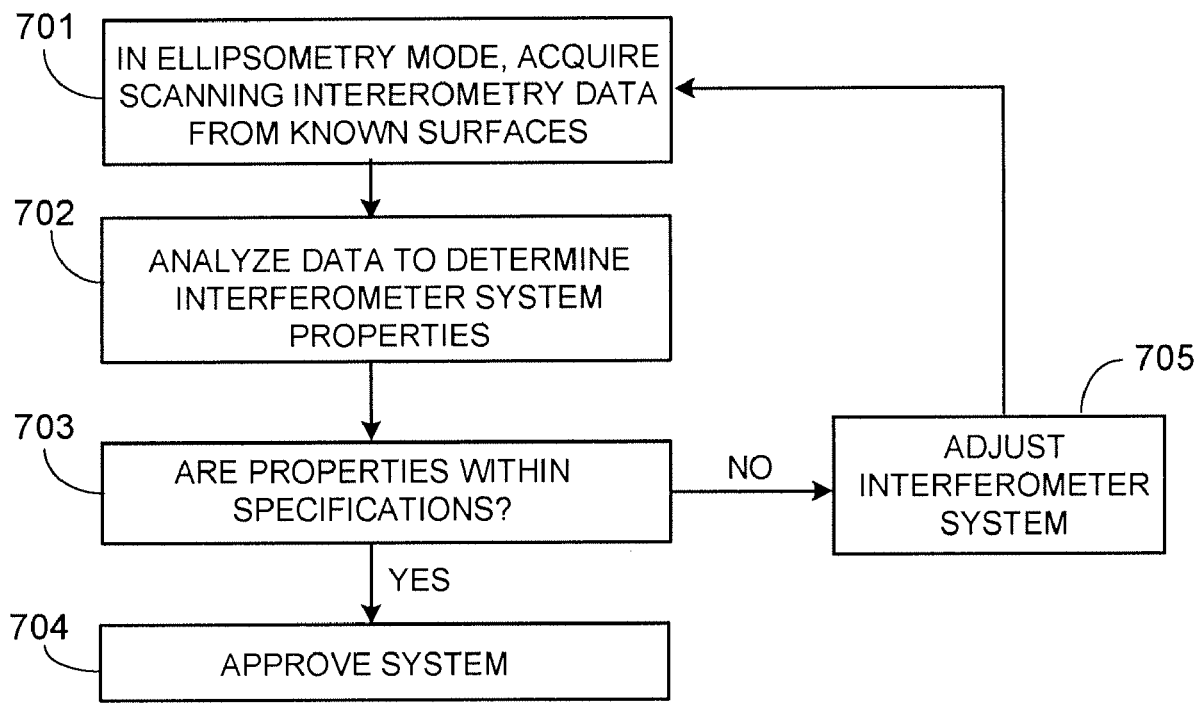
FIG. 7 shows a flow-diagram for monitoring the properties of an interferometry system.

For example, referring to FIG. 7, in one embodiment, the above described techniques are used to monitor the quality of an interferometry system in production. In step 701 using, for example, the above described methods, an interferometry system operates in an ellipsometry (e.g. pupil plane) mode to acquire scanning interferometry data suitable to provide calibration information. In step 702, the data are analyzed to determine one or more properties of the interferometry system (e.g. illumination source spectrum, intensity variations at the pupil plane of an interference objective, etc). In step 703, the determined properties are compared to manufacturer specifications. If the properties are within the specified ranges, the method moves to step 704, approving the system (e.g. for eventual sale, or to move on to another production stage). If the properties are not within the specified ranges the method moves instead to step 705, where the interferometry system is adjusted (e.g. one or more components are replaced or modified). In some embodiments, the manner of adjustment may be based, at least in part, on information about system properties determined in step 702. The method then returns to step 701, and repeats as necessary.

Figure 8:
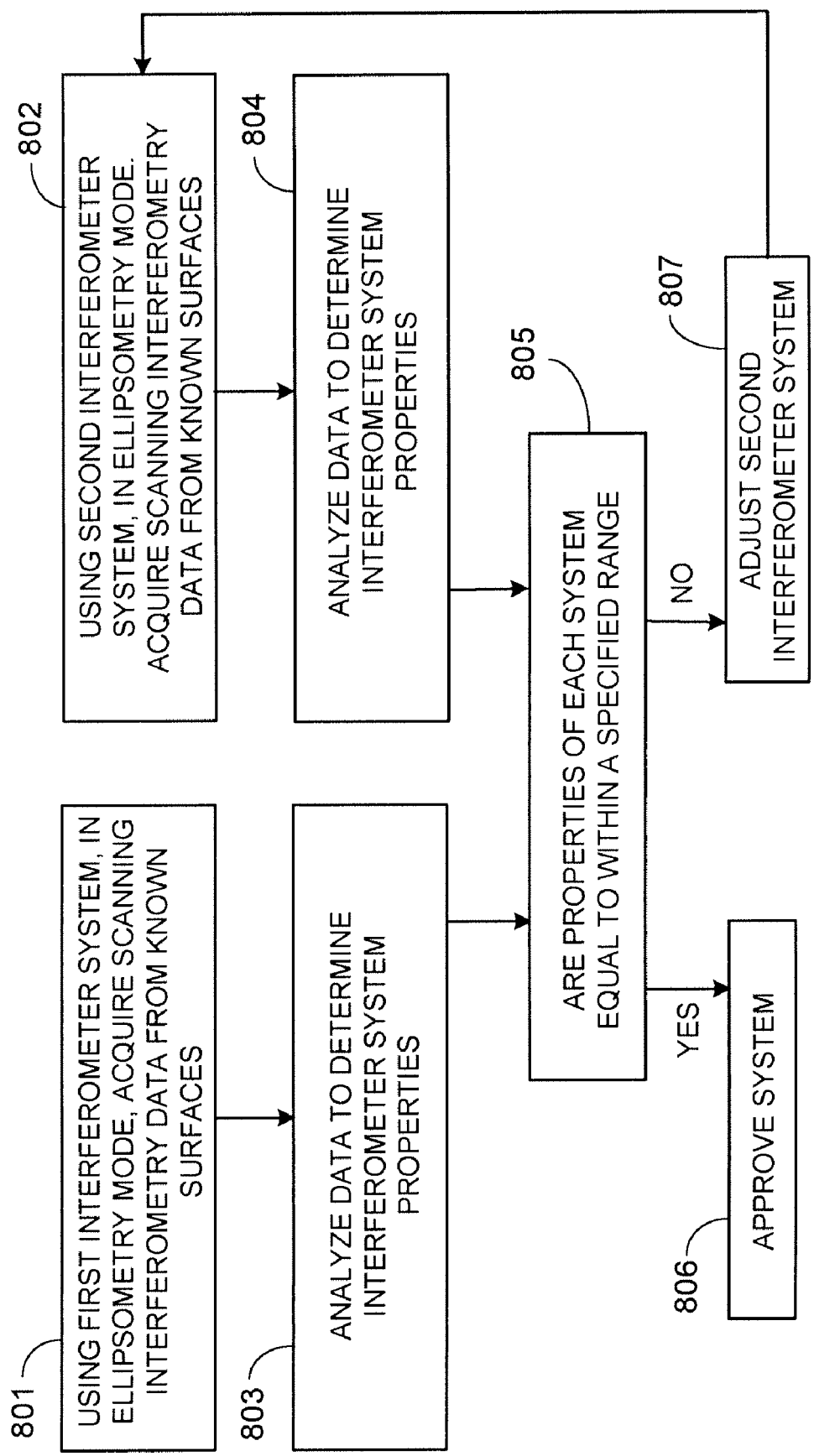
FIG. 8 shows a flow-diagram for comparing the properties of two interferometry system.

Similarly, in the embodiment show in FIG. 8, two interferometry systems are "matched" to have the same properties. This allows for uniform measurements across multiple interferometry systems. In steps 801 and 802 using, for example, the above described methods, a first and second interferometry system operates in an ellipsometry (e.g. pupil plane) mode to acquire scanning interferometry data suitable to provide calibration information. In steps 803 and 804, the data from the respective interferometry systems are analyzed to determine one or more properties of the respective systems. In step 805, the determined properties are compared to determine if they match within a specified range. If so, the method moves to step 806, approving the systems as well matched. If not, the method moves to step 807, and the second interferometry system is modified in an attempt to bring its properties within range. Modification may include, for example, replacing, modifying, or moving one or more optics, the illumination source, or any other element of the interferometry system. After the modification, the method returns to step 802, and steps 802, 804, 805, and 807 are repeated until the systems are well matched. Note that in some embodiments, both systems may be modified to attain a match.

Examples of interferometer adjustments used in the above described techniques include:
replacing beamsplitter components to equalize optical paths in test and reference legs
replacing or adjusting compensator optical elements to minimize chromatic aberrations
adjusting position of optical elements in the illumination, imaging or interferometer optics to minimize wavefront aberrations
adjusting beamsplitter or reference mirror tip and tilt
swapping optical components and/or sub-assemblies to achieve any of the goals listed above. In some embodiments, an interferometry system is adapted to include a test station used to characterize a sub-component of an instrument. For instance, system 100, as shown in FIG. 1, could be modified to allow interference objective 106 or light source 102 to be swapped out and replaced by similar sub systems. This allows the system to be used to characterize objectives and/or light sources to be used on distinct microscope systems.

Signal Modeling

As discussed in more detail below, it is often desirable to model the interference signals that would be measured by an interferometry system for a model measurement object. The accuracy of such a model signal will, in general, depend on how well the model Incorporates the properties of the interferometry system. In the following we describe how an accurate model can be generated using the system characterization functions derived above.

We first describe generally a physical model for the scanning interferometry signal acquired in a profiling mode.

The object surface has height features h which we wish to profile over an area indexed by lateral coordinates x, y. The stage provides a smooth, continuous scan $\zeta$ either of the interference objective or, as shown, of the object itself. During the scan, a computer records intensify data $I_{\zeta,h}$ for each image point or camera pixel in successive camera frames. Note that the key dependencies of the intensity $I_{\zeta,h}$ on the scan position and surface height are indicated by subscripts—a notation that we shall employ throughout.

A proper physical model of the optics can be very elaborate, taking into account the partial coherence of the light source, polarization mixing in the interferometer, the imaging properties of high-NA objectives, and the interaction of electric field vectors at high angles of incidence and in the presence of discontinuous surface features. For convenience, we simplify the model by assuming fully random, linear or circular polarization and diffuse, low-coherence extended sources. Modeling the interference signal simplifies to adding up the contributions of all of the ray bundles passing through the pupil plane of the objective and reflecting from the object surface at an incident angle $\alpha$.

The interference contribution for a single ray bundle through the optical system is proportional to $$g_{\beta,k,\zeta,h} = R_{\beta,k} + X_{\beta,k} + 2\sqrt{R_{\beta,k} Z_{\beta,k}} \cos[2\beta k n_0(h-\zeta) + (\nu_{\beta,k} - \omega_{\beta,k})]. \quad (12)$$

where $X_{\beta,k}$ is the effective object intensity reflectivity, including e.g. the effects of the beamsplitter, and $R_{\beta,k}$ is the effective reference reflectivity, including both the beamsplitter and the reference mirror. Note that this calculation is performed for a specific linear polarization stat. The contributions from multiple polarizations are calculated the same formula and simply summed. The index of the ambient medium is $n_0$, the directional cosine for an incident angle $\alpha$ is $$\beta = \cos(\alpha) \quad (13)$$

and the wavenumber for the source illumination is $$k = (2\pi/\lambda) \quad (14)$$

The sign convention for the phase causes an increase in surface height to correspond to a positive change in phase. The phase term has a contribution $\omega_{\beta,k}$ for the object path, in the interferometer, including thin film effects from the object surface, and a contribution $v_{\beta,k}$ for the reference path, including the reference mirror and other optics in the objective.

The total interference signal integrated over the pupil plane is proportional to $$I_{\zeta,h} = \int_0^\infty \int_0^1 g_{\beta,k,\zeta,h} U_\beta V_k \beta d\beta dk \tag{15}$$

where $U_\beta$ is the pupil plane light distribution and $V_k$ the optical spectrum distribution. The weighting factor $\beta$ in Eq. (15) follows from a $\cos(\alpha)$ term attributable to the projection angle and a $\sin(\alpha)$ term for the diameter of the annulus of width $d\alpha$ in the pupil plane;

$$\cos(\alpha)\sin(\alpha)d\alpha = -\beta d\beta \tag{16}$$

Here we assume that the objective obeys the Abbé sine condition. Finally, the integration limits over all incident angles implies $$0 \leq \beta \leq 1 \tag{17},$$

and the spectrum integration over all wavenumbers $0 \leq k \leq \infty$.

In a frequency domain analysis (FDA), we first calculate the Fourier Transform of the interference intensity signal $I_{\zeta,h}$. For the literal (non-numerical) analysis we shall use the unnormalized Fourier integral $$q_{K,h} = \int_{-\infty}^\infty I_{\zeta,h} \exp(iK\zeta)d\zeta \tag{18}$$

where K is the spatial frequency, e.g. in cycles per µm. To this end, we combine the definition of the Fourier Transform Eq.(17) with the interference signal Eq.(15) into the following formula for the predicted FDA spectrum:

$$q_{K,h} = \int_{-\infty}^\infty \int_0^\infty \int_0^1 g_{\beta,k,\zeta,h} \exp(iK\zeta) U_\beta V_k \beta d\beta dk d\zeta \tag{19}$$

The above described formalism may be recast to provide a model signal expressed in terms of the system characterization functions described above. Optimized forms of the model signal exist when using these functions. For example for the linearly polarized illumination case we can express the complex spectral components of the modeled signal in terms of the characterization parameters as $$q(K, h) = \exp(iKh)\int_{K/2}^\infty \tag{20}$$

$$\begin{Bmatrix} \int_0^{2\pi} D_L(\alpha_{K,k}, \theta) \\ \left((\cos\theta)^2 rp(\alpha_{K,k}, \lambda_k) - (\sin\theta)^2 \tau(\alpha_{K,k}, \lambda_k) rs(\alpha_{K,k}, \lambda_k)\right) \dots \\ \exp(i\tilde{A}(\alpha_{K,k}, \lambda_k, \theta))d\theta \end{Bmatrix}$$

$$\frac{V(\lambda_k)K}{2k^2}dk$$

where:

$$\alpha_{K,k} = \arccos(K/2k)$$

$$\lambda_k = 2\pi/k \tag{21}$$

Note that the model includes a user-defined height offset parameter h that allows controlling the position of the object surface within the height range covered by the signal trace.

For the circularly polarized case we have the simpler form:

$$q(K, h) = \exp(iKh)\int_{K/2}^\infty \overline{(rp(\alpha_{K,k}, \lambda_k) - \tau(\alpha_{K,k}, \lambda_k)rs(\alpha_{K,k}, \lambda_k))} \tag{22}$$

$$\exp(-iA(\alpha_{K,k}, \lambda_k)) \dots \frac{D_c(\alpha_{K,k})V(\lambda_k)K}{2k^2}dk$$

where a possible azimuthal dependence of the phase function, disappears using Eq.(11)

Figure 6A:
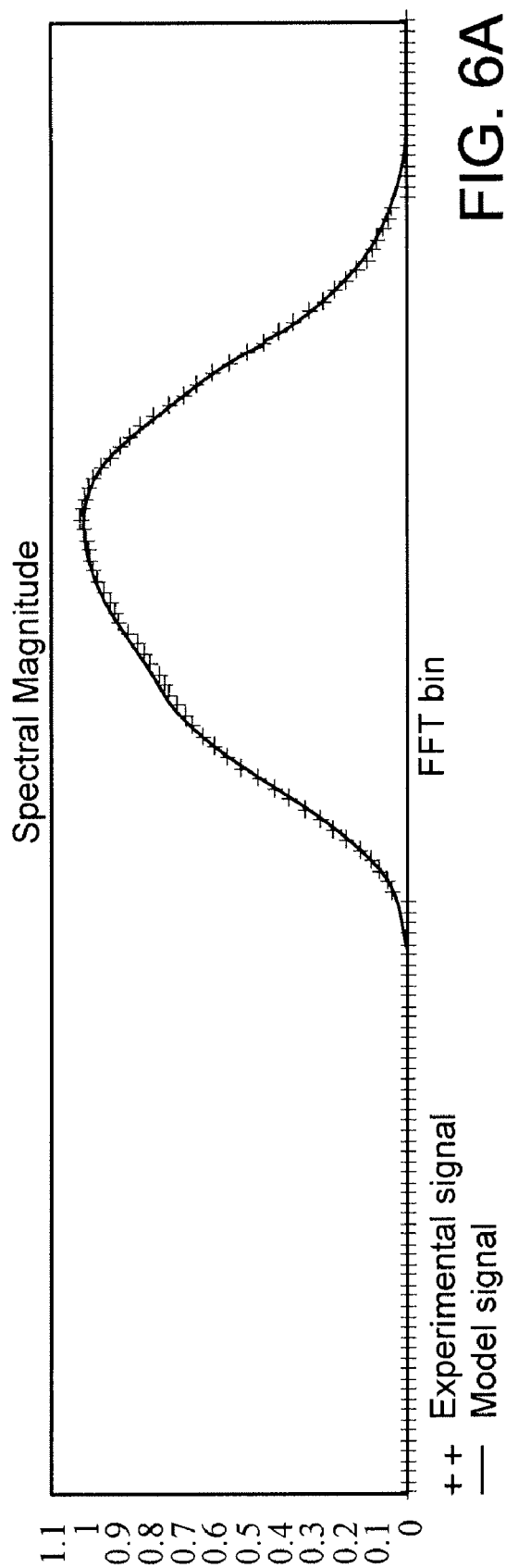
FIG. 6a shows a comparison of the spectral magnitude of a measured interference signal and a model interference signal in the spatial frequency domain.
Figure 6B:
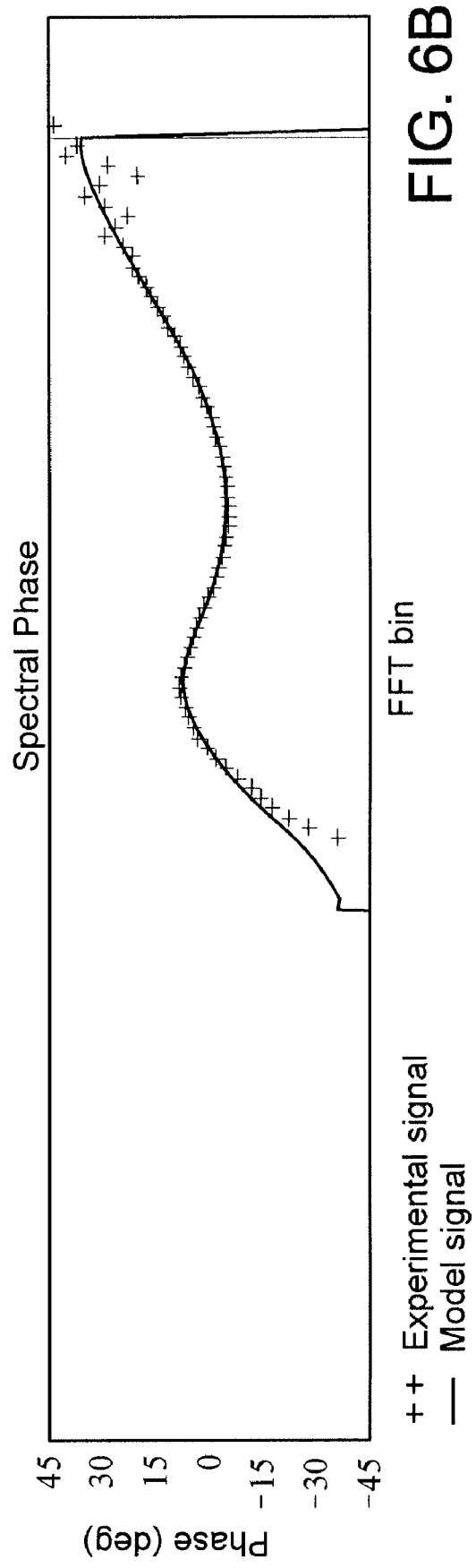
FIG. 6b shows a comparison of the spectral phase of a measured interference signal and a model interference signal, in the spatial frequency domain.
Figure 6C:
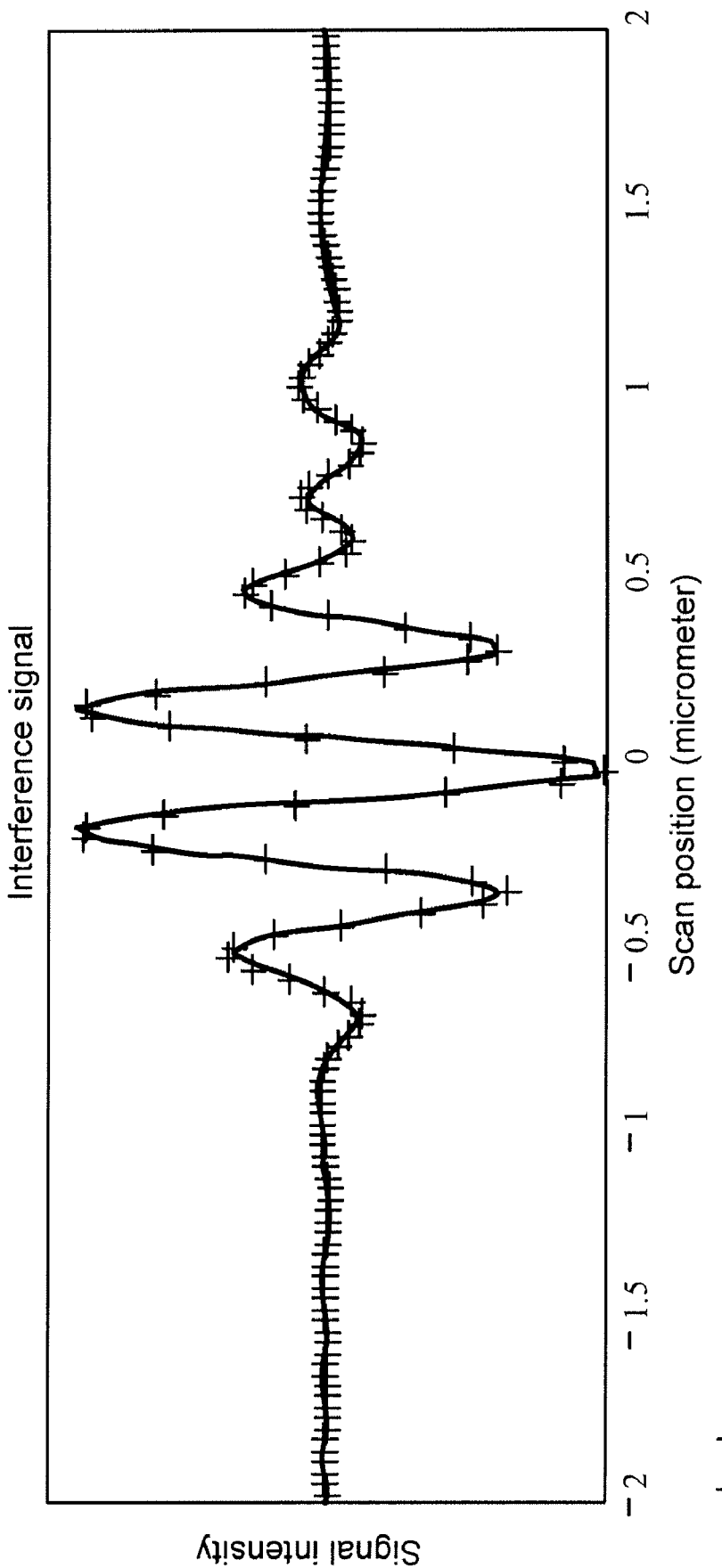
FIG. 6c shows a comparison of the signal intensity of a measured interference signal and a model interference signal, as a function of scan position.

Accurate model signals can be generated by using the above described techniques to acquire the values of the characterization. For example, FIG. 6a shows the magnitude of the complex spectrum q(K,h) calculated using Eq. 20 in the ease of a high-magnification interference microscope used with a broadband light, source and linearly polarized illumination light to characterize the surface of a bare silicon surface. The plot also shows the magnitude of an experimental spectrum captured with the same interference microscope in a topography measurement mode. Note the excellent agreement of the model with the experimental data. Similarly, FIG. 6b compares the theoretical phase spectrum 603 with the experimental phase spectrum 604 for the same experiment. Note again the excellent agreement of the model with the experimental, data. Finally, FIG. 6c compares the Fourier transform of the model spatial frequency spectrum into the scan domain, and the scan domain experimental signal. Once again the agreement is excellent.

Note that Equations 20 and 22 are expressed in terms of complex reflectivities for s- and p-polarized light. However, in cases where a test object includes under-resolved features (i.e., features with characteristic sizes below or near the optical resolution of interferometry system), incident light in a given polarization state may be mixed into the orthogonal polarization state of light reflected from the test object. Such mixing may be modeled using, for example, Maxwell's equations and Rigorous Coupled Wave Analysis techniques. Once the mixing has been accounted for, expressions identical to equations 20 and 22 may be used as accurate model signals. For example, the techniques described below may be applied to objects with under-resolved features by using reflectivities rp and rs which have been corrected for the mixing effect. In all other respects the formalism remains unchanged.

Model-based Measurement of an Unknown Object

In the following, we describe how the model signal generating techniques described above are applied in techniques for measuring an unknown object (e.g. measuring a surface profile of the unknown object). Referring to FIG. 9, in some embodiments, object 126 includes four surface regions, 901, 902, 902, and 904 each with different film properties (e.g. differing film, structures, materials, surface roughness, unresolved features, etc.). For example, referring to FIG. 9b, a cross section of region 901 shows that the region includes a film stack etched to form grating 908. In some embodiments this grating 908 is underresolved (i.e. below or near the optical resolution of interferometry system 100). These complicated structures will affect the interference signals measured by interferometry system 100 in the profiling mode. Accordingly, a topography map generated from the measured signals will show errors across the four regions.

In particular, in many embodiments, this distortion will take the form of erroneous height offsets which depend on characteristics of the measured region, and so vary from region to region.

For example, when in the profiling mode of operation, the material and/or film stack properties can affect the interferometry system's measured surface height profile. For example, if a test object with regions of copper separated by dielectric regions on a semiconductor wafer, the measurement light incident on the surface will experience a phase change on reflection (PCOR) which depends of Ore material properties of the region upon which it is incident. PCOR are material dependent and affect the topography measurement. For example, copper regions appear lower than they truly are with respect to the dielectric regions. This affects the topography measurement. Similar dependencies and height offsets occur with regions of the surface which have thin film stacks.

Figure 10A:
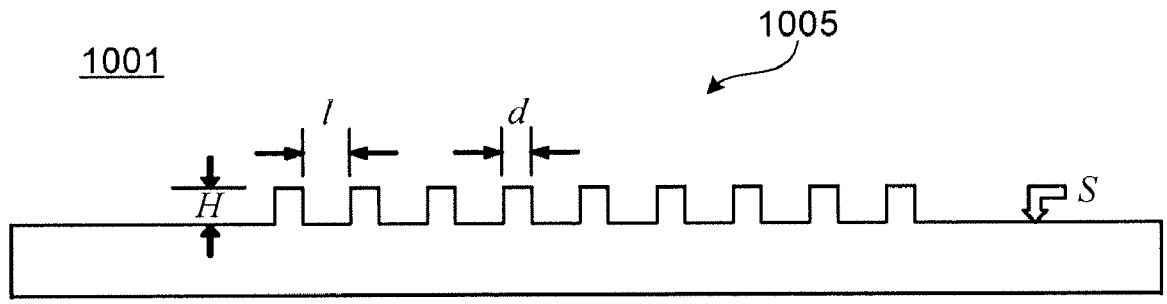
FIG. 10a shows an object including an underresolved surface feature.
Figure 10B:
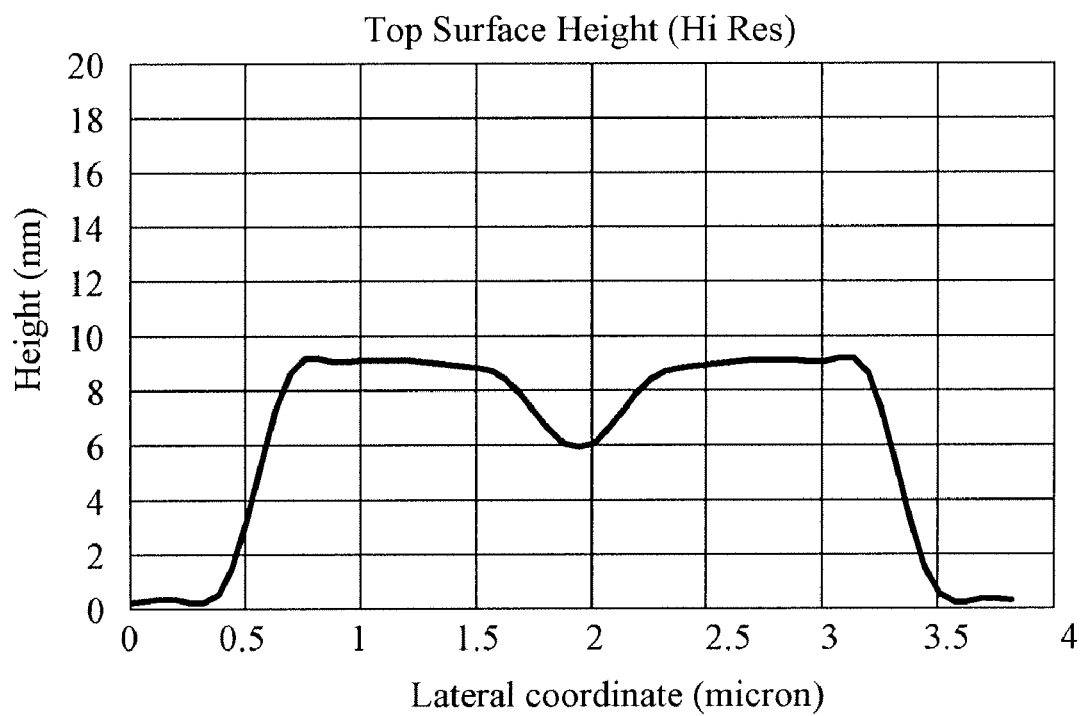
FIG. 10b shows a calculated profile of an object including an underresolved surface feature.

Further, even small surface structures can degrade the accuracy of profile measurements. For example. FIG. 10a shows another example of a surface region 1001 having a grating structure 1005. The unresolved surface features have a height H above an adjacent surface S, a separation l and a width d. The height H is also referred to herein as a modulation depth for the patterned structure. Again, by "underresolved" it is meant that the individual features are not folly separated in the surface profile image. FIG. 10b illustrates a predicted surface profile for the unresolved features on surface region 1001, for a visible-wavelength interferometer (560 nm center wavelength, 110 nm bandwidth full width half maximum) and an objective NA of 0.8. The surface structures are unresolved, resulting in an apparent measured surface profile that does not resemble at all the actual surface structure. For this calculation, the height H=20 nm, the separation l=200 nm and a width d=120 nm.

Figure 10C:
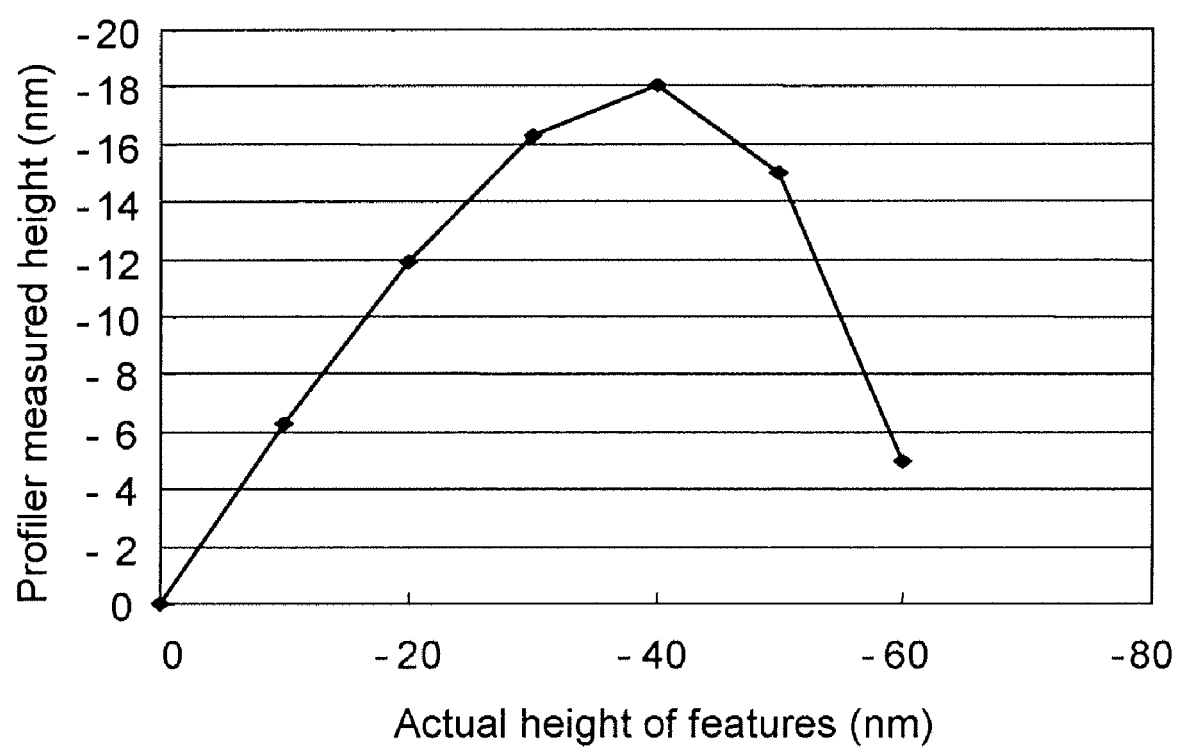
FIG. 10c shows a plot of a predicted height offset as a function of surface profile height for an object including an underresolved surface feature.

FIG. 10c shows how the unresolved measured profile of 10b varies as a function of the actual height H of the features. Noteworthy is that the relationship between the measured and true height is complicated and even negatively correlated above 40 nm. This latter phenomenon can be explained as the difficulty in coupling light into the narrow, sub-wavelength trenches.

One approach to overcoming the errors in a profiling measurements due to variations in material, film stack, surface features, etc., across a surface of interest is to compare measured profiling interference signals to synthetic signals generated based on models of the surface (and/or regions thereof) of interest. By matching the experimental signals the synthetic signals, one determines a model surface which corresponds well to the actual surface.

Figure 11:
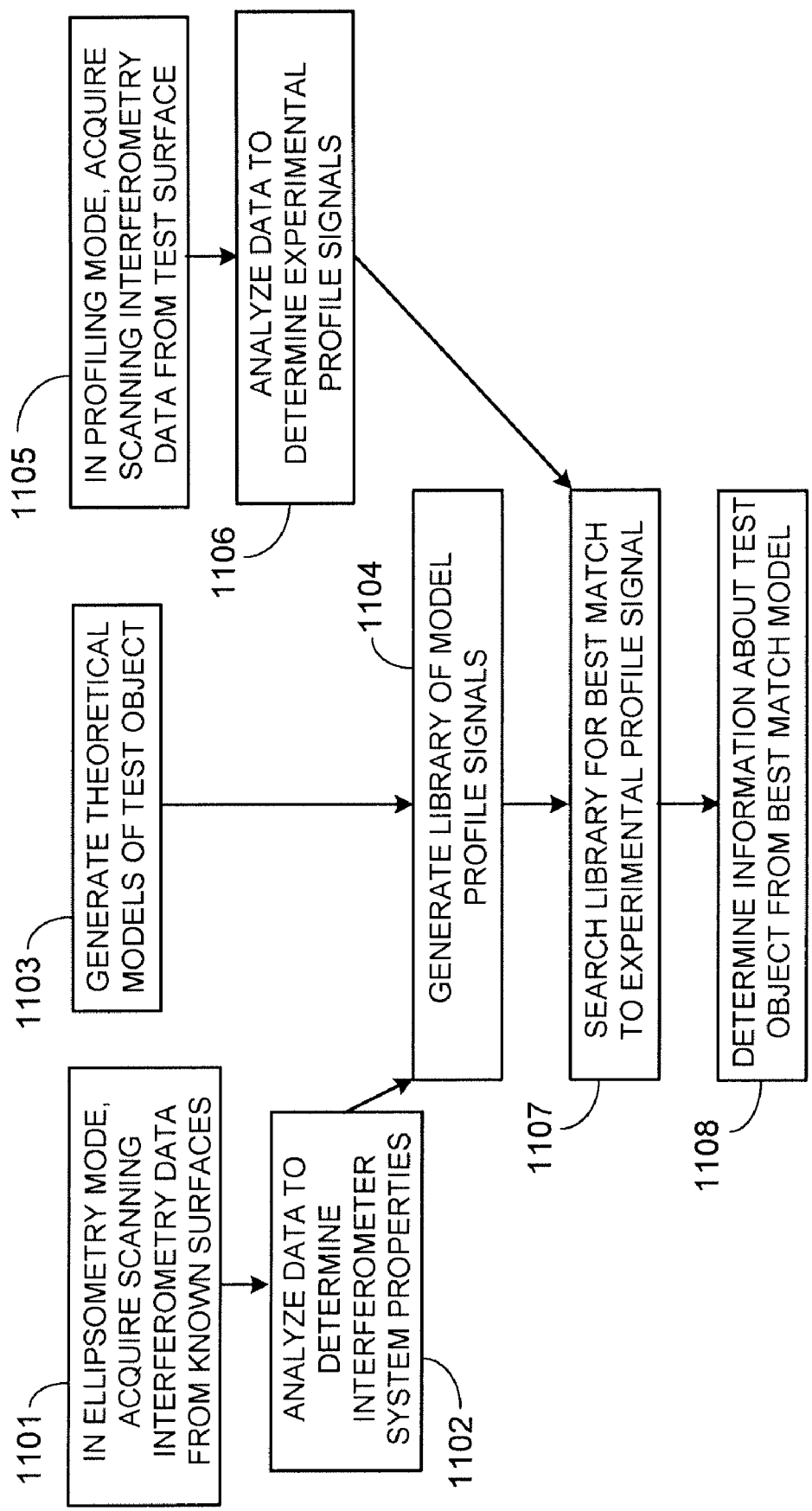
FIG. 11 shows a flow-diagram for model-based measurement technique.

For example, FIG. 11 shows a flow diagram of an embodiment of such a method. As described in detail above, an interferometry system is used, in an ellipsometry mode, to determine the interferometry system's characterization parameters (e.g. $J(\alpha, \lambda_u, \theta)$, $\tau(\alpha, \lambda)$, and/or parameters derived there from). Theoretical models are generated (using, e.g. Eqs. (20) or (22)) corresponding to a variety of materials, film stacks, underresolved features, etc., potentially present at the area of interest on the object. The system characterization information 1101, 1102 and the theoretical 1103 models are combined 1104 to generate a library of synthetic signals corresponding to the various models of the surface. Experimental interference signals collected 1105, 1106 by the interferometry system in the profiling mode are then compared 1107 in the space or frequency domain to the library entries. The best library match 1108 identifies the model surface which corresponds well to the actual surface of interest. This model provides information about the material or film stack present on the object surface, such as for example thickness and refractive index. The best match signal library is defined for a specific object height within the library signal trace. This information is used to calculate the location of—for example—an air/material interface of the object surface within, the experimental signal trace. This provides the ability to report surface topography that is not affected by the presence of dissimilar materials or film stacks.

Figure 12:
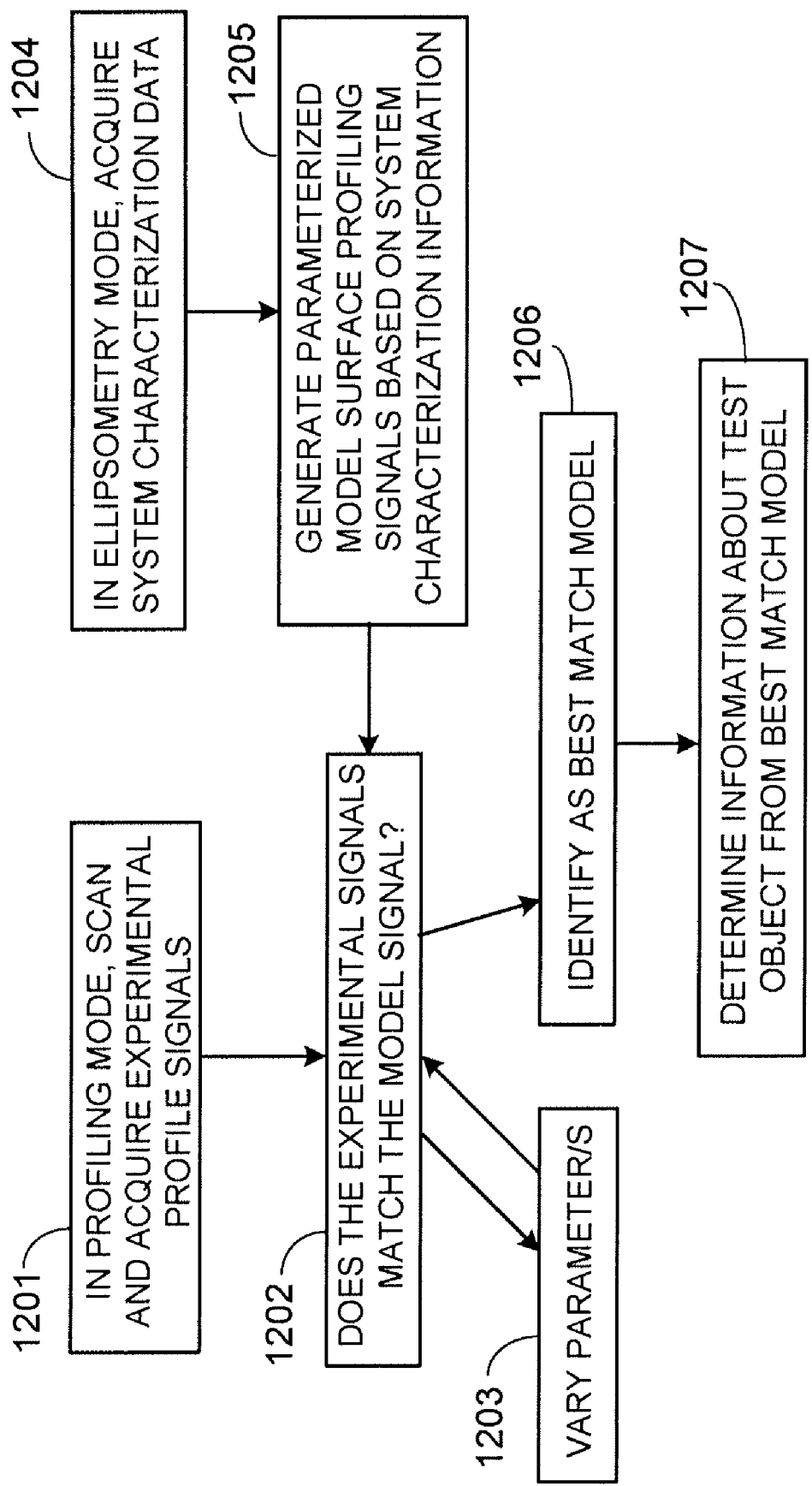
FIG. 12 shows a flow-diagram for another model-based measurement technique.

In a further embodiment, as shown in the flow diagram of FIG. 12, experimental signals collected in the topography mode are matched to model signals by iteratively refining the model parameters that describe the material or film stack present on the object surface. As described in detail above, an interferometry system is used, in an ellipsometry mode, to determine the interferometry system's characterization data 1204. A parameterized model of the surface of interest is generated 1205. One or more properties of the model surface can be adjusted by changing a corresponding parameter. For example, a parameterized model of region 901 of FIG. 9b might include parameters which could adjust one or more of grating pitch 905, grating width 905, film stack thickness 907, etch depth 909 and surface height 101. Synthetic interferometry signals are generated based on the characterization information and model parameterized signal.

In a profiling mode, the interferometry system obtains 1201 experimental interference signals. The experimental signals are compared 1202 to the synthetic signals generated from the parameterized model, while the parameters are varied 1203 to determine a good match between the signals. The model with the best match parameters will correspond well to the experimentally measured surface structure. Accordingly, this model can be analyzed to determine 1207 information about the surface of interest. For example, the best fit parameters give a good estimate for the physical properties (e.g. film thickness, surface, height, etc) to which they correspond.

Figure 13:
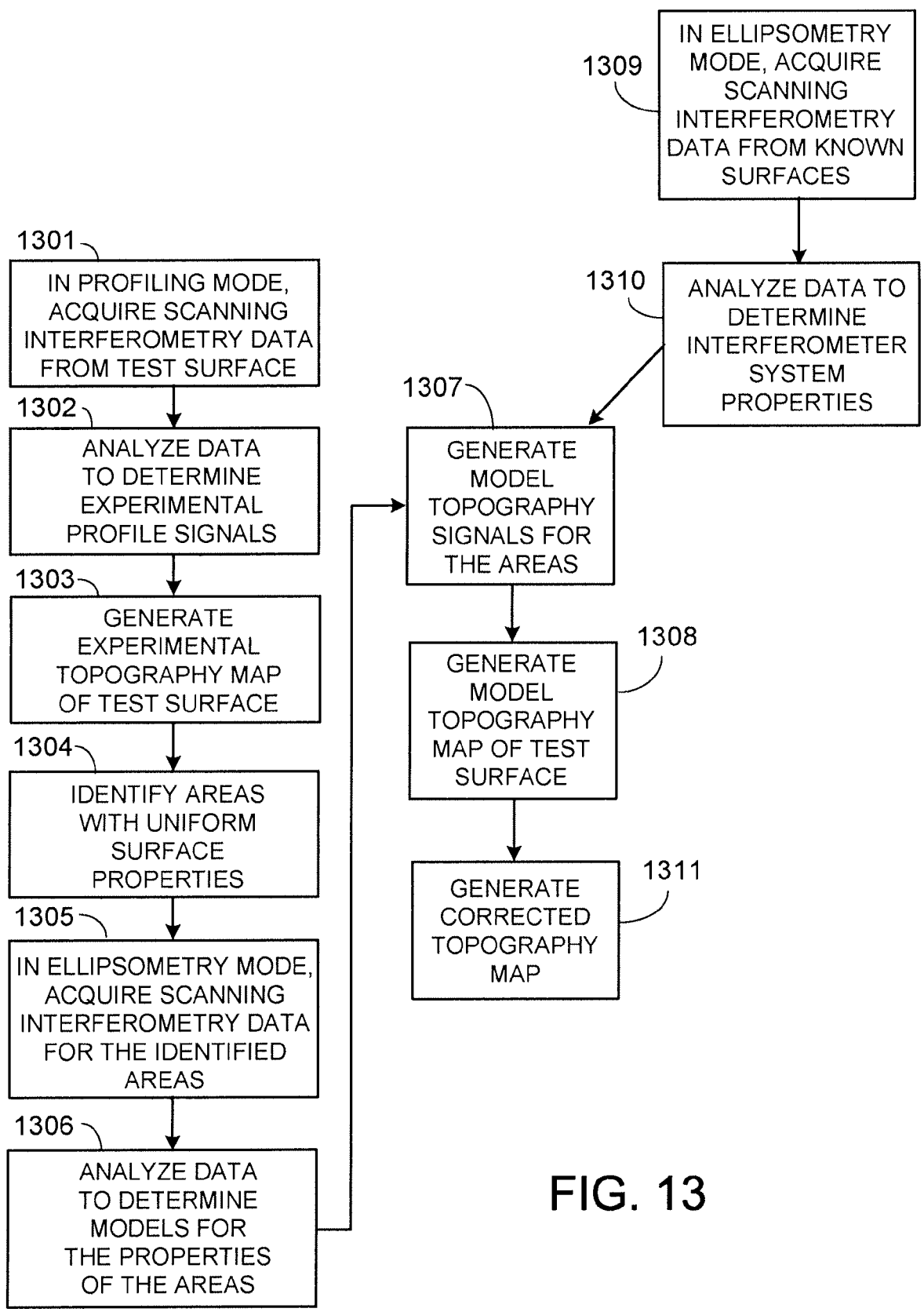
FIG. 13 shows a flow-diagram for another model-based measurement technique.
Figure 14:
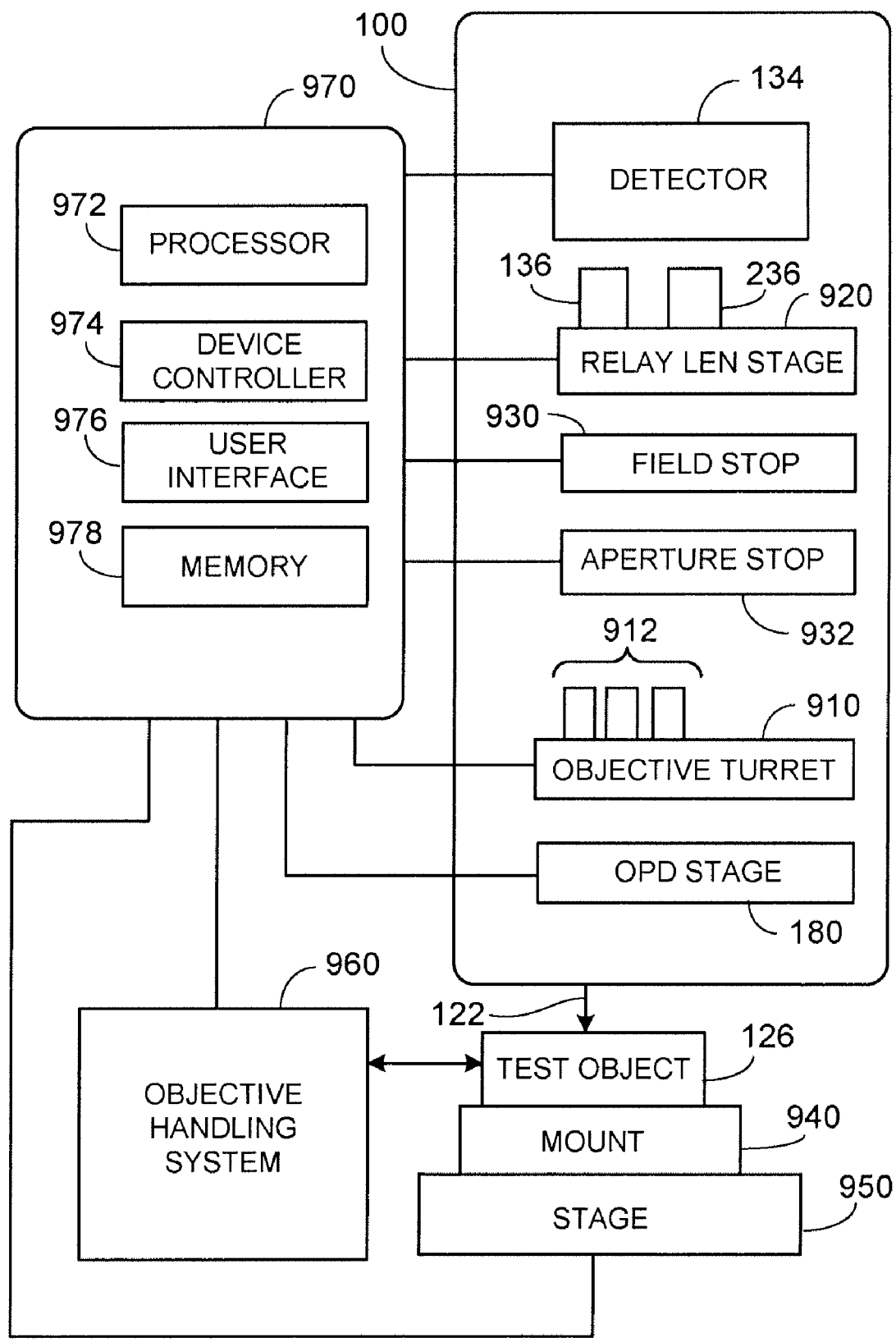
FIG. 14 is a schematic diagram of another embodiment for interferometry system 100.

A further embodiment, as shown in the flow diagram of FIG. 13, combines both the ellipsometry and profiling measurement modes of the interferometry system for the purpose of generating a topography map that is corrected for the effects of dissimilar characteristics such as material properties, film stacks, underresolved structures, etc., across the surface of the object of interest.

The profiling measurement mode is used 1301 to capture a topography map 1302, 1303 of the object surface. As described above, this map may include errors caused by variations in surface characteristics. The ellipsometry mode is used to determine these characteristics at specific locations on the object surface where the characteristics are uniform within the measurement area 1303.

Such areas may be determined by, for example, analyzing an intensity or topography image of the object surface to identify the locations where the ellipsometry mode must be used. In typical cases the layout of the object features are known a priori. One can then use pattern matching techniques to locate the areas of interest. Alternatively, other types of processing of the topography interference data can yield information about areas on the object surface having similar optical properties. For instance, the mean interferometry signal intensity provides a means of estimating object reflectivity and its variations across the surface. Another example attribute is the so-called phase-gap (phase measured at the location of maximum fringe modulation). Yet another attribute is the phase or magnitude non-linearity of the spectrum of the interference signal. A map of any one of these quantitative attributes can be used in practice to locate uniform regions to be characterized in ellipsometry mode, in various embodiments, a motorized stage may be used to position the object accordingly by moving either the sample or the interferometer to make ellipsometry measurements at suitable locations of interest.

Figure 9A:
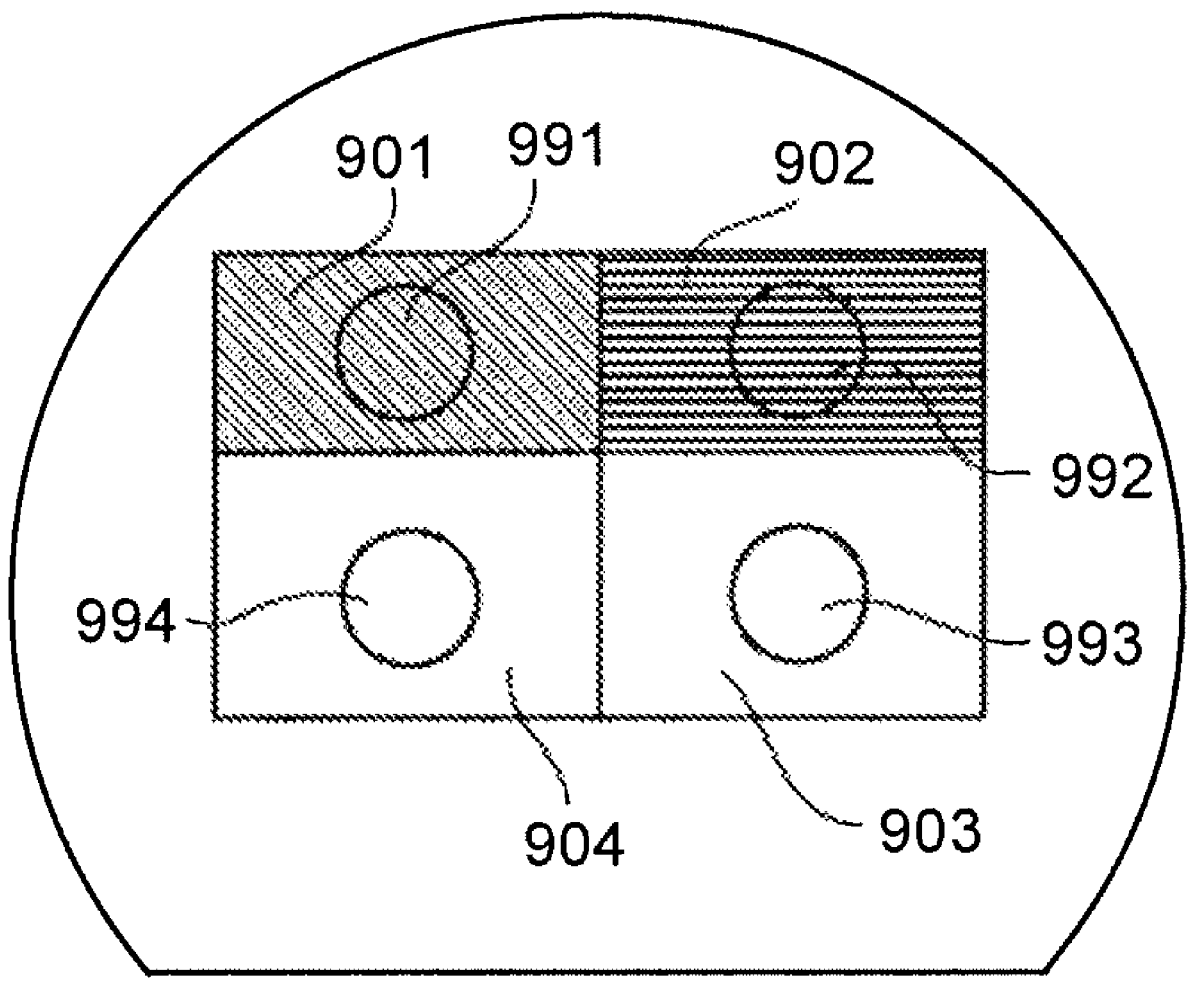
FIG. 9a shows a top-down view of a test object.
Figure 9B:
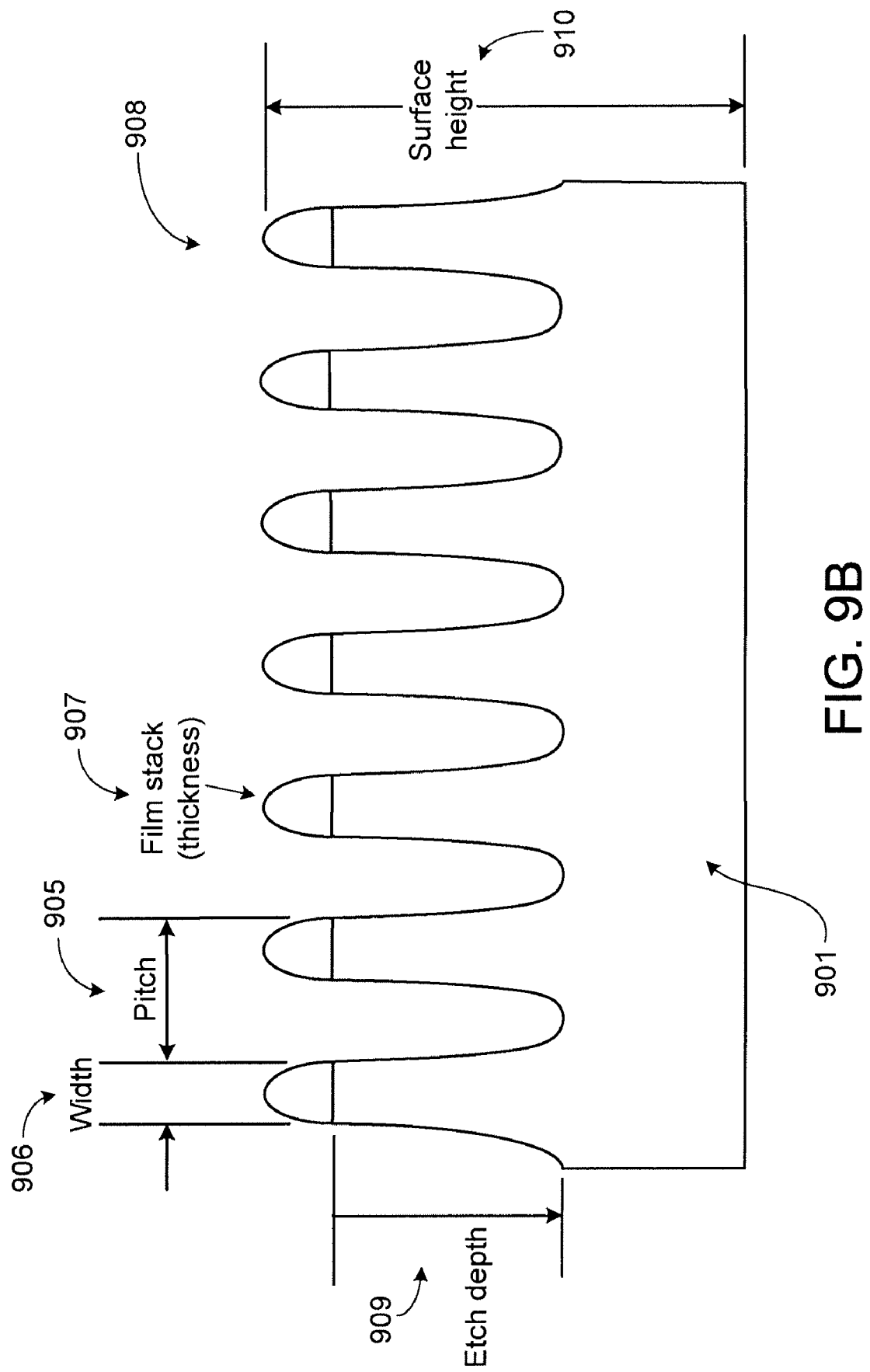
FIG. 9b shows a cross section of a portion of a test object.

For example, referring to object 126 of FIG. 9a, measurement locations 991, 992, 993, and 994 would be suitable for characterizing surface regions 901, 902, 903, and 904 respectively.

As described above, output of the measurement 1304 provides the complex reflectivity of the surface over multiple wavelengths, angles of incidence, and polarizations. This information can provide 1305 a model that captures the optical properties of the object, such as a material model or film stack model, and/or underresolved feature model including information such as refractive indices, thicknesses, etc.

Returning to FIG. 13, one can then input 1306 the measured reflectivity information into, for example, either Eq. 21 or Eq.(22) along with 1308, 1309 system characterization information to generate a model signal corresponding to the signal that would be measured at this location in topography mode. Height offset h in the model signal is chosen equal to the height measured experimentally at the chosen surface location. This model signal is then processed with the algorithm used to create the topography map, resulting in a model height for the chosen location. The resulting model height at the chosen location, is then, compared to the measured height of the object surface at that location. The difference of these two values corresponds to a height offset induced in the topography map by the optical properties of the object in the corresponding area of the surface. Tins height offset is then subtracted from the topography map within the sub-region. This process is repeated for each of sub-regions 901, 902, 903, and 904 on the object'surface. The end result 1310 is a topography map of the object surface that is free of material- or film-induced offsets. Note that, as discussed above, the various ellipsometry measurement described above can be processed to provided estimates offer example material optical properties and film stack thickness(es), which can be output along with, or in addition to the corrected topography map.

Alternatively, for each location, the height offset h can be chosen arbitrarily. For example, for a location made up of a thin film covering a substrate, h might be chosen such, that the portion of the signal corresponding to the air/film interface is located at the center of the scan). The signal may then be processed using the profiling algorithm to determine the location of the air/film interface. The difference between the location output by the algorithm and the location set by the choice of the parameter h will correspond to the height offset which should be used to correct the profile map at that location.

The corrected topography profile can be obtained in an additional way. Note that the ellipsometry measurement of a given location contains information about both the test object, and the properties of the interferometer (e.g.; intensity, spectral, and phase information about the illumination at the pupil plane). In some eases, it is preferable to use this information directly, rather than use the characterization functions appearing in Eqs. 20 and 22. For example, in the case where the intensity $D_L(\alpha, \theta)$ has been modeled, as described above, using only a few Zernike polynomials, some intensity information will be lost. The equivalent information may be obtained more accurately from the ellipsometry data.

The difficulty in obtaining interferometry characterization data from the ellipsometry measurement is that the measured interference signals are complicated by effects related to surface height of the test object. For example, referring to FIG. 4 (lower plot), the phase spectrum of a Fourier transformed will, in general, be surface height dependent. However, the magnitude spectrum is translation invariant along the direction of scan, and therefore does not depend on surface height.

Thus, for a given location, an accurate model signal maybe obtained as follows. The experimentally measured ellipsometry signals are acquired and Fourier transformed. To generate a model signal, the frequency spectrum of the experimental signal corresponding to each detector element is stripped of its phase information which is replaced by the argument of the complex coefficient shown in Eq. 23, for linearly polarized light and in Eq. 24 for circularly or unpolarized light, $$\overline{((\cos\theta)^2 rp(\alpha,\lambda) - (\sin\theta)^2 \tau(\alpha,\lambda) rs(\alpha,\lambda))} \exp(-iA(\alpha,\lambda)) \exp(iKh), \quad (23)$$

$$\overline{(rp(\alpha,\lambda) - \tau(\alpha,\lambda) rs(\alpha,\lambda))} \exp(-iA(\alpha, \lambda)) \exp(iKh), \quad (24)$$

The modified signals are summed, thereby providing a model signal of the form of Eqs. 20 or 22, with the height invariant experimental information taking the place of one or more system characterization functions. As before, the resulting model signal depends on surface height only through an arbitrary surface height offset h, and thus may be analyzed using the techniques described above to determine a surface height correction for a topography map.

Additional Embodiments for Profiling

Figure 15:
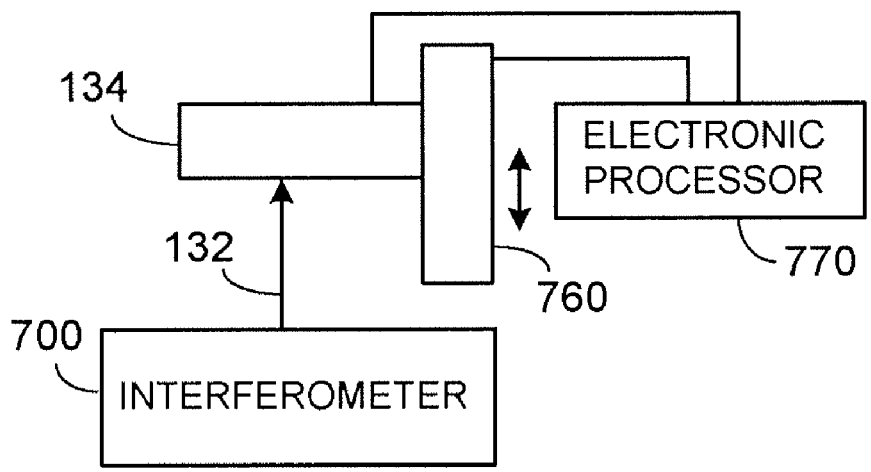
FIG. 15 is a schematic diagram of another embodiment for interferometry system 100.
Figure 16:
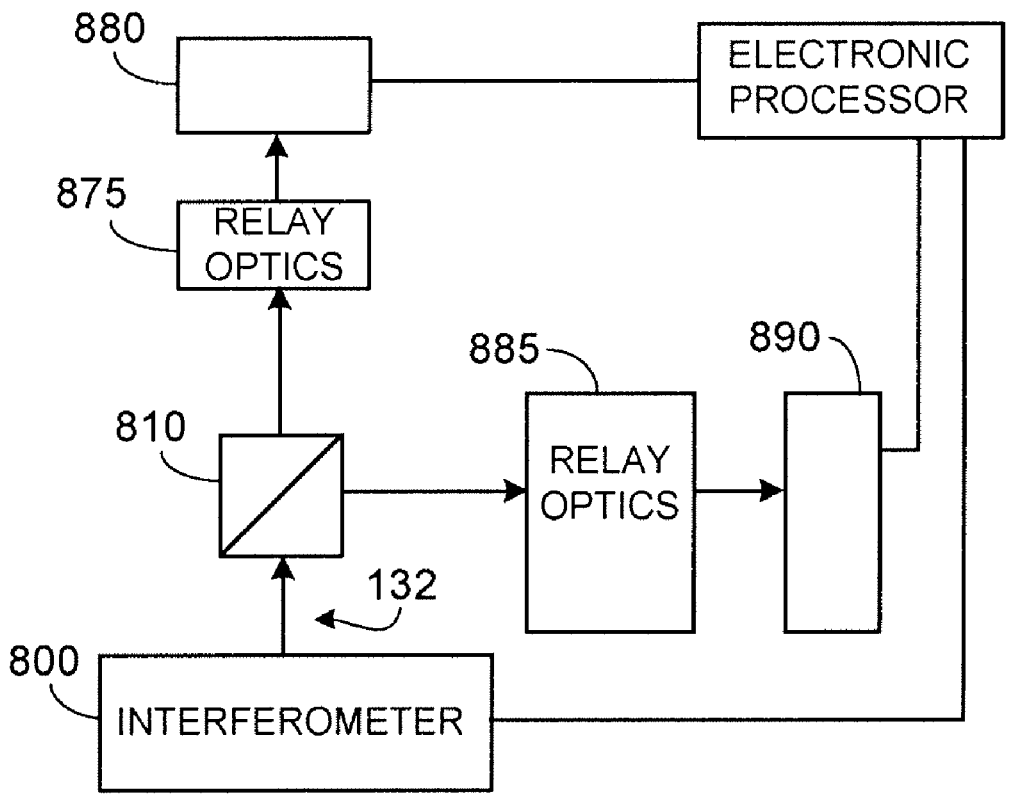
FIG. 16 is a schematic diagram of yet another embodiment for interferometry system 100.

Instead of switching out relay lens 136, in further embodiments, for example, the relay lens can be left alone and detector 134 can be translated to a position where the test surface is in focus. This is shown schematically in FIG. 15, which shows detector 134 coupled to a motorized translation stage 760 under the control of electronic processor 770 to adjust the detector position for receiving combined light 132 relative to the rest of the interferometry system 700. The translation stage allows the system to switch between a first position corresponding to the ellipsometry mode, in which the pupil plane is imaged to the detector, and a second position corresponding to the profiling mode, in which the test surface is imaged to the detector.

Figure 17:
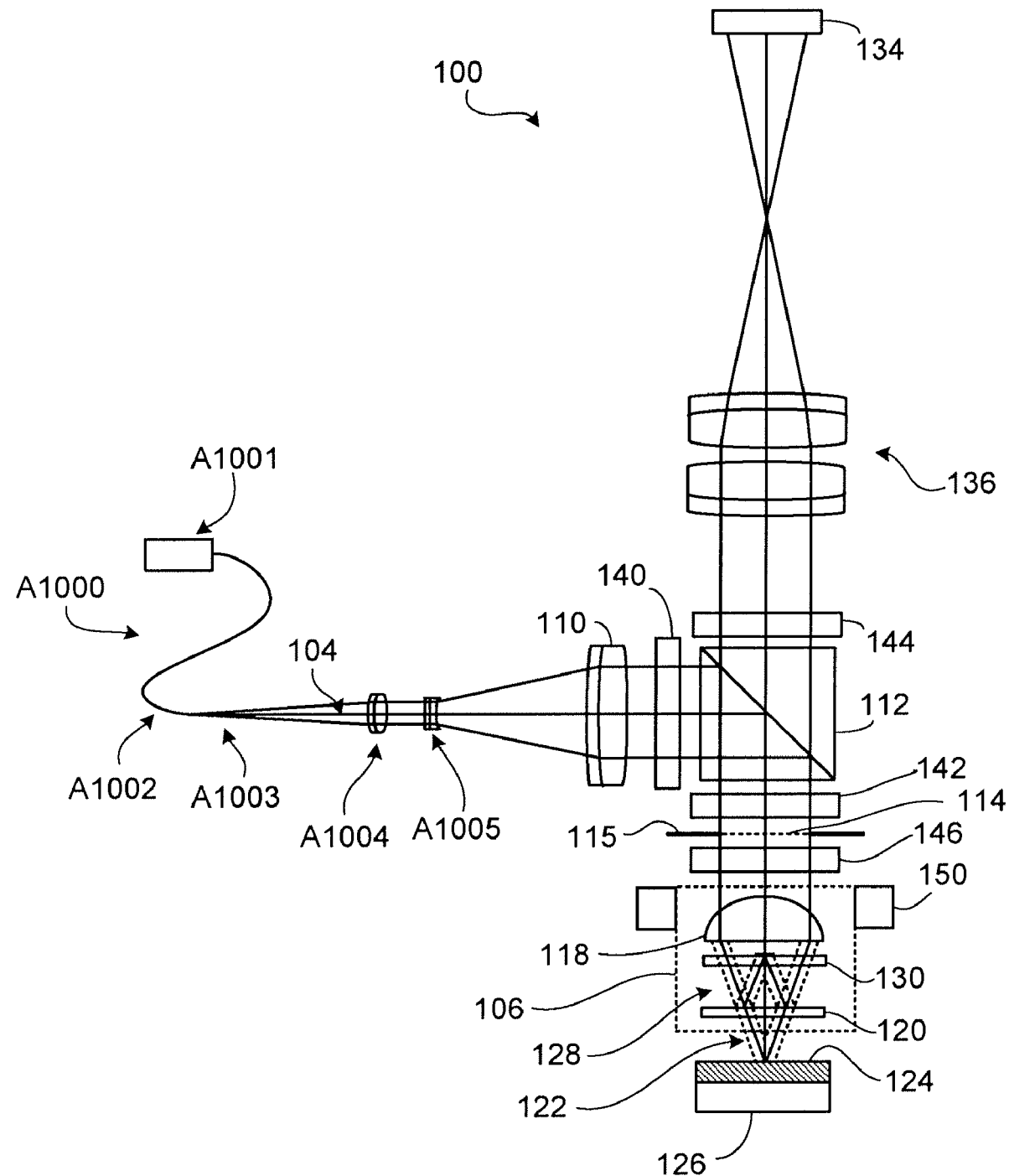
FIG. 17 is a schematic diagram of interferometry system 100 configured to operate in an ellipsometry mode, featuring broadband, spatially coherent illumination.

In yet a further embodiment, shown schematically in FIG. 17 a beam splitter 810 can split the combined light 132 received from the rest of the interferometry system 800 into two channels with two corresponding multi-element detectors 880 and 890, with one channel using relay optics 875 to image pupil plane 114 to the first detector 880 to provide the ellipsometry mode measurement and the other channel using relay optics 885 to image the test surface to the second detector 890 to simultaneously provide the profiling mode measurement. Both detectors are coupled to electronic processor 870, which analyze the detector images as described above.

Various combinations of these approaches are also possible. For example, the system can include optics that image the pupil plane to a first portion of a common electronic detector and image the test surface to a second portion of the common electronic detector. In this case, the different portions of the common electronic detector can be considered to be separate detectors.

Applications

The above described techniques have wide applicability. For example, the system can be used in a semiconductor process for tool specific monitoring or for controlling the process flow itself. In the process monitoring application, single/multi-layer films are grown, deposited, polished, or etched away on unpatterned Si wafers (monitor wafers) by the corresponding process tool and subsequently the thickness and/or optical properties are measured using the interferometry system disclosed herein (for example, by using the ellipsometry mode, the profiling mode, or both). The average, as well as within wafer uniformity, of thickness (and/or optical properties) of these monitor wafers are used to determine whether the associated process tool is operating within targeted specification or should be retargeted, adjusted, or taken out of production use.

In the process control application, latter single/multi-layer films are grown, deposited, polished, or etched away on patterned Si, production wafers by the corresponding process tool and subsequently the thickness and/or optical properties are measured with the Interferometry system disclosed herein (for example, by using the ellipsometry mode, the profiling mode, or both). Production measurements used for process control typical include a small measurement site and the ability to align the measurement tool to the sample region of interest. This site may consists of multi-layer film stack (that may itself be patterned) and thus requires complex mathematical modeling in order to extract the relevant physical parameters. Process control measurements determine the stability of the integrated process flow and determine whether the integrated processing should continue, be retargeted, redirected to other equipment, or shut down entirely.

Specifically, for example, the interferometry system disclosed herein can be used to monitor the following equipment: diffusion, rapid thermal anneal, chemical vapor deposition tools (both low pressure and high pressure), dielectric etch, chemical mechanical polishers, plasma deposition, plasma etch, lithography track, and lithography exposure tools. Additionally, the interferometry system disclosed herein can be used to control the following processes: trench and isolation, transistor formation, as well as interlayer dielectric formation (such as dual damascene).

Broadband Spatially Coherent Illumination

In some embodiments, the test object is illuminated with spatially coherent light. Light is said to be spatially coherent when the oscillation of the electromagnetic field is substantially correlated (i.e., has a substantially fixed phase relationship) for points spatially separated in a direction transverse to the direction of propagation. See *Encyclopedia of Laser Physics and Technology* available at http://www.rp-photonics.coherence.html and E. Hecht, *Optics, Second Edition,* pp. 516-517, Addison Wesley, 1987, For example, in a spatially coherent light beam, the electromagnetic field at points on a cross-section of the beam will oscillate in a correlated way. As will be described below, the use of spatially coherent light allows for diffraction limited or near-diffraction limited illumination of areas on the test object. In certain embodiments, this allows for illumination and measurement of small, well-defined regions of the test surface. Further, in some embodiments, the spatially coherent illuminating light can be spectrally broadband, allowing for wavelength resolved measurements, as described above.

For example, referring to FIG. 17, interferometry system 100 operates in an ellipsometry mode, as shown in FIG. 1, but with a broadband spatially coherent illumination system 1000 (described in more detail below), replacing elements 102, 108, and 138. In the present embodiment, light source 1001 is coupled to optical fiber 1002 to generate spatially coherent input light 104 (the chief rays of which are indicated by solid lines). Input light 104 is spatially coherent across face 1003 of fiber 1002. As indicated by chief rays, input light 104 is collimated by collimator lens 1004. The collimated beam is expanded by expander lens 1005 to match the size of objective pupil aperture stop 115, re-collimated by lens 110, and directed to pupil plane 114 of interference objective 106. For example, in embodiments where shape of the light beam is Gaussian (or nominally Gaussian) the beam waist may be imaged pupil plane 114.

Beam splitter 120 separates input light 104 into test light 122, which is directed to a test surface 124 of a test object 126, and reference light 128, which reflects from reference surface 122. Objective lens 118 focuses the test and reference light to the test and reference surfaces, respectively. The reference optic 130 supporting reference surface 122 is coated to be reflective only for the focused reference light, so that the majority of the input light passes through the reference optic before being split by beam splitter 120.

After reflecting from the test and reference surfaces, the test and reference light are recombined by beam splitter 120 to form combined light 132, which is transmitted by beam splitter 112 and relay lens 136 to form an optical interference pattern on an electronic detector 134. The intensity profile of the optical interference pattern across the detector is measured by different elements of the detector and stored in an electronic processor (not shown) for analysis. In this ellipsometry configuration, the pupil, plane 114 is imaged onto the detector. In the present embodiment, relay lens 136 images different points on the pupil plane 114 to corresponding points on detector 134.

Illumination system A1000 provides spatially coherent illumination over a broad band of wavelengths (e.g., an emission spectrum having a full-width, half-maximum of more than 50 nm, or preferably, even more than 100 nm). Such broadband, spatially coherent illumination can be provided by a number of types of sources.

For example, in some embodiments, optical fiber A1002 is a so called "monomode" fiber. A monomode fiber supports only a single (or, in some cases, a few) spatial mode for light propagating along the fiber. See, e.g., *Encyclopedia of Laser Physics and Technology,* available at http://www.rp-photonics.com/single_mode_fibers.html. Thus, when light source 1001 is coupled to the fiber, output light 104 contains primarily light in the supported spatial mode. The light across output face 1003 is thereby well correlated, yielding spatially coherent output light 104. Monomode fibers are typically capable of supporting a single spatial mode over a range of wavelengths. Thus, when light source A1001 is a broadband source (e.g. a broadband or "white light" LED, an LED array, a pulsed or broadband laser source, etc) which inputs light over a spectral range within the range of supportable wavelengths, the light output by monomode fiber 1002, will be both broadband and spatially coherent.

In some embodiments, the optical fiber 1002 includes a photonic bandgap material (e.g. photonic crystal material) or other nonlinear material which is capable of supporting spatially coherent light over a very broad range of wavelengths (e.g. up to hundreds of nanometers or more), thereby allowing for very broadband spatially coherent illumination. See, e.g. *Encyclopedia of Laser Physics and Technology,* available at http://www.rp-photonics.com/photonic_crystal_fibers/html. Such systems are sometimes said to provide "supercontinuum" illumination. In some such embodiments, fiber A1002 may also be a monomode fiber, supporting a single (or few) spatial mode for light over a very wide range of wavelengths (e.g. a range spanning wavelengths from the infra-red and above to the ultraviolet and below). See, e.g. *Encyclopedia of Laser Physics and Technology,* available at http://www.rp-photonics.com/supercontinuum_generation.html.

In some embodiments, fiber A1002 contains nonlinear material which acts to further broaden the spectral range of light input into the fiber. Nonlinear effects (e.g. Raman scattering or four wave mixing) occur as the light propagates along the fiber, producing light at wavelengths other than those present in the input light. In some such embodiments, light source A1001 may be a relatively narrowband source, with spectral broadening provided by fiber A1002 to produce broadband output light 304.

In further embodiments, illumination system A1000 includes a resonant cavity capable of producing a spatially coherent output beam. For example, light source 1001 may include a resonant cavity pumped by a source (e.g. a laser, LED, or LED array) to excite the cavity to resonate at a single (or a few) spatial mode of the cavity. The output of the cavity will thereby be spatially coherent. In some such embodiments, fiber A1002 may be removed, with input light 104 deriving directly from light source A1001 (e.g., as the output beam of the resonant cavity). In some embodiments the cavity may include a filter which acts to limit the number of spatial modes which are supported by the resonant cavity.

Note that coherent illumination differs from cases in which the measurement object is illuminated by light with a low degree of spatial coherence (e.g., when using a spatially incoherent extended source imaged at pupil plane 114 to provide Koehler illumination). For example, in typical applications (e.g. those where some minimum intensity is required at the detector for a useful measurement), a spatially incoherent illuminating light beam will produce a large spot size at test object 126 (e.g., a spot size significantly wider than the diffraction spot of interference objective 106).

In the present embodiment, however, test light 122 is spatially coherent, and may be focused to a small spot size at test object 126. The focused beam at test object 126 is, in this case, the convolution of the geometrical point spread function of interference objective 106 by its diffraction spot. For spatially coherent pupil plane illumination, the geometrical point spread is defined as the irradiance distribution at the object of point sources in pupil plane 114, when all diffraction effects are ignored. In typical embodiments, the geometric point spread of interference objective 106 depends on, for example, optical aberrations in the objective, and can be reduced or even eliminated using correction techniques know in the art. The diffraction spot is, on the other hand, the irradiance distribution at object 126 due to diffraction effects including, for example, effects of apertures, obscurations, etc along the objective.

For a well corrected objective illuminated with spatially coherent light, the spot size at test object 126 can approach or essentially equal the width of the diffraction spot at the test object. For an objective with a high numerical aperture objective (e.g., about 0.7 or greater, or about 0.9 or greater), the diffraction spot can be, for example, a fraction of a micrometer for the central lobe of the illumination spot. Thus, in the presently described embodiment and using the techniques described above, interferometry system 100, in an ellipsometry mode, can determine angle, wavelength, and polarization resolved information (e.g. complex reflectance information) for a small, well defined region of test surface 124 of test object 126. Such a measurement can be repeated over multiple areas on test surface 124. For example, complex reflectance measurements taken at multiple test spots across test surface 124 can be analyzed to map out properties of test object 126 such as film thickness, material type, index of refraction etc. Such information could, for example, be used to improve a surface profile measurement made using interferometry system 100 operating in a profiling mode.

Note that spatially coherent illumination differs from illumination by light with a low degree of spatial coherence in another respect. For spatially incoherent light, light diffusely reflected from test surface 124 will combine incoherently (i.e. with a random phase relationship) at detector 134. Thus, over a few periods, the intensity of the combined electromagnetic field at detector 134 corresponding to the diffusely reflected light will average to zero. As typical detection times are generally much longer than a few periods, the diffusely reflected light will therefore have no contribution to the interference signal measured by detector 134.

This is not the case for spatially coherent illumination. Instead, diffusely reflected light will combine coherently at detector 134. The intensity of the diffusely reflected light will therefore not average to zero, and so may contribute to the interference signal measured by detector 134. In some applications, (e.g. when the test surface does not have substantial lateral variations across the measurement spot) this contribution will be negligible. In such cases, the measurement model of Eq. 3 remains a good approximation, allowing the use of the analysis techniques described above. In cases where the contribution due to diffuse reflection to the measured interference signal is significant, Eq. 3 is no longer a good approximation. However, such signals may still be analyzed using, for example, model based techniques in which the measured signal is compared to, for example, model signals calculated using the full Maxwell's equations and/or exemplary signals based on known reference samples. Examples of such techniques are be found in U.S. Provisional Patent Application No. 60/870,748, entitled APPARATUS AND METHOD FOR MEASURING CHARACTERISTICS OF SURFACE FEATURES and filed on Dec. 22, 2006, which is incorporated herein by reference.

In some embodiments, interferometry system 100 includes an optical element (e.g. a diffuser) which may be selectively switched into the beam path to reduce the spatial coherence of the illuminating light. In some applications it is desirable to switch between spatially coherent illumination focused to provide a small measurement spot at test object and spatially incoherent illumination which illuminates a larger portion of test object. In some cases (e.g. when measuring a slightly rough or patterned object), a larger measurement spot may be useful to improve the statistics of the measurement. For example one may provide the option of Koehler illumination by imaging the spatially coherent light source (i.e. fiber face 1003) onto a diffuser (not shown) placed within aperture stop 115 of interference objective 106.

Although the presently described embodiment describes the use of broadband spatially coherent illumination source with interferometry system 100 in an ellipsometry mode, it is to be understood that such a source can be used similarly in a variety of other modes, including the profiling mode described above.

ADDITIONAL EMBODIMENTS

The embodiments shown in FIGS. 1 and 3 implement an interference objective of the Mirau-type, in which the beam splitter in the interference objective directs the reference light back along the optical axis for the test light. In other embodiments, interferometry system 100 can instead use a different type of interference objective, such as a Michelson objective, in which the beam splitter directs the reference light away from the optical axis of the test light (e.g., the beam splitter can be oriented at 45 degrees to the input light so the test light and reference travel at right angles to one another). In such cases, the reference surface can be positioned outside of the path of the test light.

In another embodiment, the interference objective can be of the Linnik-type, in which the case the beam splitter is positioned prior to the objective lens for the test surface (with respect to the input light) and directs the test and reference light along different paths. A separate objective lens is used to focus the reference light to the reference lens. In other words, the beam splitter separates the input light into the test and reference light, and separate objective lenses then focus the test and reference light to respective test and reference surfaces, ideally the two objective lenses are matched to one another so that the test and reference light have similar aberrations and optical paths.

Additional interferometer configurations are also possible. For example, the system can be configured to collect test light that is transmitted through the test sample and then subsequently combined with reference light. For such embodiments, for example, the system can implement, a Mach-Zehnder interferometer with dual microscope objectives on each leg.

In some embodiments the interferometer may be a scanning interferometer that uses a spherical measurement wavefront, such, as that described in U.S. Pat. No. 6,714,307 entitled "MEASUREMENT OF COMPLEX SURFACE SHAPES USING A SPHERICAL WAVEFRONT" and filed Jul. 3, 2002, the contents of which are incorporated herein by part.

The light source in the interferometer may be any of: an incandescent source, such as a halogen bulb or metal halide lamp, with or without spectral bandpass filters; a broadband laser diode; a light-emitting diode; a combination of several light sources of the same or different types; an arc lamp; any source in the visible spectral region; any source in the IR spectral region, particularly for viewing rough surfaces & applying phase profiling; and any source in the UV spectral region, particularly for enhanced lateral resolution. For broadband applications, the source preferably has a net spectral bandwidth broader than 5% of the mean wavelength, or more preferably greater than 10%, 20%, 30%, or even 50% of the mean wavelength. For tunable, narrow-band applications, the tuning range is preferably broad (e.g., greater than 50 nm, greater than 100 nm, or greater than even 200 nm, for visible light) to provide reflectivity information over a wide range of wavelengths, whereas the spectral width at any particular setting is preferable narrow, to optimize resolution, for example, as small as 10 nm, 2 nm, or 1 nm. The source may also include one or more diffuser elements to increase the spatial extent of the input light being emitted from the source.

In some embodiments the interferometer can be configured such that some or all of the interferometer's optical elements are reflective elements. For example, in applications where input light is in the UV or extreme UV (EUV) spectral, refractive optical elements using typical materials would absorb a substantial amount of the light in such applications all refractive elements in the interferometer could be replaced by reflective elements such as, for example, curved mirrors.

Furthermore, the various translations stages in the system, such as translation stage 150, may be; driven by any of a piexo-electric device, a stepper motor, and a voice coil; implemented opto-mechanically or opto-electronically rather than by pure translation (e.g., by using any of liquid crystals, electro-optic effects, strained fibers, and rotating waveplates) to introduce an optical path length variation; any of a driver with a flexure mount and any driver with a mechanical stage, e.g. roller bearings or air bearings.

The electronic detector can be any type of detector for measuring an optical interference pattern with spatial resolution, such as a multi-element CCD or CMOS detector.

In various embodiments, interferometry system 100 outputs measurement information to, for example, a user display, a printer, a machine-readable medium, or storage device, a electronic controller, etc. In some embodiments, the output data can automatically control a further device or devices (e.g., integrated circuit processing and/or metrology tools).

Software

The analysis steps described above can be implemented in computer programs using standard programming techniques. Such programs are designed to execute on programmable computers or specifically designed integrated circuits, each comprising an electronic processor, a data storage system (including memory and/or storage elements), at least one input device, and least one output device, such as a display or printer. The program code is applied to input data (e.g., images from the detector) to perform the functions described herein and generate output information (e.g., refractive index information, thickness measurement(s), surface profile(s), etc.), which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis and control functions described herein.

A number of embodiments of the invention have been described. Nevertheless, it will be understood that various modifications may be made without departing from the spirit and scope of the invention.

What is claimed is:

1. An interferometry method, comprising:

directing test light to a first calibration surface over a range of illumination angles and combining the test light emerging back from the first calibration surface with reference light to form an interference pattern, wherein the test light from the first calibration surface and the reference light are derived from a common source;

directing at least a portion of the combined light from the first calibration surface to a multi-element detector so that different elements of the detector correspond to different illumination angles of the first calibration surface by test light;

directing test light to a second calibration surface different from the first calibration surface over a range of illumination angles and combining the test light emerging back from the second calibration surface with reference light to form an interference pattern, wherein the test light from the second calibration surface and the reference light are derived from the common source;

directing at least a portion of the combined light from the second calibration surface to the multi-element detector so that different elements of the detector correspond to different illumination angles of the second calibration surface by the test light; and determining information about an interferometry system based on interference signals measured by the different elements of the detector for the test light emerging from the first and second calibration surfaces and other information about the first and second calibration surfaces, wherein:

the information about the interferometry system comprises information corresponding to at least one of a spectral distribution of the common source, a relative attenuation of a polarization state perpendicular to the plane of incidence compared to a polarization state parallel to the plane of incidence, a variation of the spectral distribution of the illumination across a pupil plane of the interferometry system, a variation of the mean intensity of the illumination across a pupil plane of the interferometry system, a variation of the phase of the illumination across a pupil plane of the interferometry system, and a variation of the spectral intensity of the illumination across a pupil plane of the interferometry system.

2. The method of claim 1, wherein the other information about the first and second calibration surfaces comprises information about the reflectivity of the first and second calibration surfaces.

3. The method of claim 1, wherein the first calibration surface comprises: bulk silicon, an oxide layer on silicon, a dielectric layer or layers on a substrate, an opaque metal layer or layers on a substrate, a solid surface of a metal, a solid surface of a dielectric material.

4. The method of claim 1, further comprising:
comparing the information about the interferometry system to a standard calibration from the interferometry system; and
modifying the interferometry system based on the comparison.

5. The method of claim 1, further comprising:
comparing the information about the interferometry system to information about a second interferometry system; and
modifying one or both of the interferometry systems based on the comparison.

6. The method of claim 1, further comprising generating multiple model scanning interferometry signals based on the information about the interferometer and information about multiple models of a test object, wherein the multiple models of the test object are parametrized by a series of characteristics of the test object.

7. The method of claim 6, further comprising comparing information derivable from a scanning interferometry signal acquired by the interferometry system for a first surface location on a test object to information derivable from the multiple model scanning interferometry signals.

8. The method of claim 7, further comprising determining an accurate characteristic for the test object based on the comparison.

9. The method of claim 8, wherein the accurate characteristic is a surface height for the first surface location and/or a film thickness for the first surface location.

10. The method of claim 8, wherein the determining of the accurate characteristic comprises determining which model of the test object corresponds to an accurate one of the characteristic for the test object based on the comparison, and using the model of the test object corresponding to the accurate characteristic to calculate information about the test object.

11. The method of claim 7, further comprising comparing information derivable from the scanning interferometry signal for additional surface locations to the information derivable from the multiple model scanning interferometry signals.

12. The method of claim 7, wherein the comparing comprises using a search engine to compare the information derivable from the scanning interferometry signal acquired by the interferometry system to the information derivable from the multiple model scanning interferometry signals.

13. The method of claim 7, wherein the comparing comprises calculating one or more merit functions indicative of a similarity between the information derivable from the scanning interferometry signal and the information corresponding to each of the models.

14. The method of claim 1, further comprising
using the interferometry system to measure a test surface of a test object in a mode of operation that interferometrically profiles a topography of the test surface; and
providing a corrected profile based on the information about the interferometry system.

15. The method of claim 14, wherein the test surface is a top surface of the test object.

16. The method of claim 14, wherein the test surface is a buried surface of the test object.

17. The method of claim 14, further comprising:
determining information about one or more areas on the test surface; and
wherein the corrected profile is also based on the information about the one or more areas on the test surface.

18. An interferometry method comprising:
for each of multiple areas of a test surface on a test object having different reflectivities, using an interferometry system to measure each area in a first mode of operation that measures information about the reflectivity of the area over a range of angles and wavelengths;
using the same interferometry system to measure the test surface in a second mode of operation that interferometrically profiles a topography of the test surface over a range including at least some of the multiple areas; and
correcting the profile based on the information about the reflectivity of the multiple areas to reduce errors.

19. The method of claim 18, wherein the test surface is a top surface of the test object.

20. The method of claim 18, wherein the test surface is a buried surface of the test object.

21. The method of claim 18, wherein the profile is a thickness profile.

22. The method of claim 18, wherein the correcting comprises, for each area:
determining a height offset based on the information about the reflectivity of the area; and
adding the offset to the corresponding portion of the profile.

23. The method of claim 18, further comprising
using the same interferometry system to measure information about the reflectivity of two or more reference surfaces over a range of angles and wavelengths;
using information about the reflectivity of the two or more reference surfaces to determine information about, the interferometry system; and
wherein the correcting of the profile is further based on the information about the interferometry system.

24. The method of claim 23, further comprising:
determining additional information about the interferometer system based on the information about the reflectivity of the area over a range of angles and wavelengths; and
wherein the correcting of the profile is further based on said determined information about the interferometry system.

25. The method of claim 18, further comprising: outputting the corrected profile.

26. The method of claim 18, wherein the outputting of the corrected profile comprises outputting to one of: a user, a display, electronic storage, an electronic controller, and electronic controller configured to operate one or more devices based on information related to the profile, printed media, and electronic storage media.

27. The method of claim 18, where the outputting comprises outputting for use in semiconductor metrology measurements.

28. An interferometry system comprising:

a light source;

a multi-element detector;

an interferometer configured to:
- direct test fight to a first calibration surface over a range of illumination angles and combine the test light emerging back from the first calibration surface with reference light to form an interference pattern, wherein the test light from the first calibration surface and the reference light are derived from a common light source;
- direct at least a portion of the combined light from the first calibration surface to the multi-element detector so that different elements of the detector correspond to different illumination angles of the first calibration surface by test light;
- direct test light to a second calibration surface different from the first calibration surface over a range of illumination angles and combine the test light emerging back from the second calibration surface with reference light to form an interference pattern, wherein the test light from the second calibration surface and the reference light are derived from the light source; and
- direct at least a portion of the combined light from the second calibration surface to the multi-element detector so that different elements of the detector correspond to different illumination angles of the second calibration surface by the test light; and an electronic processor configured to:
- determine information about the interferometry system based on interference signals measured by the different elements of the detector for the test light emerging from the first and second calibration, surfaces and other information about the first and second calibration surfaces, wherein:
the information about the interferometry system comprises information corresponding to at least one of: a spectral distribution of the common source, a variation of the spectral distribution of the illumination across a pupil plane of the interferometry system, a variation of the mean intensity of the illumination across a pupil plane of the interferometry system, a variation of the phase of the illumination across a pupil plane of the interferometry system, and a variation of the spectral intensity of the illumination across a pupil plane of the interferometry system.

29. The interferometry system of claim 28, wherein the other information about the first and second calibration surfaces comprises information about the reflectivity of the first and second calibration surfaces.

30. The interferometry system of claim 28, wherein the first calibration surface comprises: bulk silicon, an oxide layer on silicon, a dielectric layer on a substrate, an opaque metal layers on a substrate, a solid surface of a metal, a solid surface of a dielectric material.

31. The interferometry system of claim 28, further comprising:
- compare the information about the interferometry system to a standard calibration from the interferometry system; and
- modify the interferometry system based on the comparison.

32. The interferometry system of claim 28, wherein the electronic processor is configured to:
- compare the information about the interferometry system to in formation about a second interferometry system; and
- modify one or both of the interferometry systems based on the comparison.

33. The interferometry system of claim 28, wherein the electronic processor is configured to:
- generate multiple model scanning interferometry signals based on the information about the interferometer and information about multiple models of a test object, wherein the multiple models of the test object are parametrized by a series of characteristics of the test object.

34. The interferometry system of claim 33, wherein the electronic processor is configured to compare information derivable from a scanning interferometry signal acquired by the interferometry system for a first surface location on a test object to information derivable from the multiple model scanning interferometry signals.

35. The interferometry system of claim 34, wherein the electronic processor is configured to determine an accurate characteristic for the test object based on the comparison.

36. The interferometry system of claim 35, wherein the accurate characteristic is a surface height for the first surface location and/or a film thickness for the first surface location.

37. The interferometry system of claim 35, wherein the determining of the accurate characteristic comprises determining which model of the test object corresponds to an accurate one of the characteristic for the test object based on the comparison, and using the model of the test object corresponding to the accurate characteristic to calculate information about the test object.

38. The interferometry system of claim 34, wherein the electronic processor is configured to compare information derivable from the scanning interferometry signal for additional surface locations to the information derivable from the multiple model scanning interferometry signals.

39. The interferometry system of claim 34, wherein the comparing comprises using a search engine to compare the information derivable from the scanning interferometry signal acquired by the interferometry system to the information derivable from the multiple model scanning interferometry signals.

40. The interferometry system of claim 34, wherein the comparing comprises calculating one or more merit functions indicative of a similarity between the information derivable irons the scanning interferometry signal and the information corresponding to each of the models.

41. The interferometry system of claim 28, wherein the interferometer system is configured to:
- to measure a test surface of a test object in a mode of operation that interferometrically profiles a topography of the test surface; and
- the electronic processor is configured to provide a corrected profile based on the information about the interferometry system.

42. The interferometry system of claim 41, wherein the test surface is a top surface of the test object.

43. The interferometry system of claim 41, wherein the test surface is a buried surface of the test object.

44. The interferometry system of claim 41, wherein the electronic processor is configured to:
- determine information about one or more areas on the test surface; and
- wherein the corrected profile is also based on the information about the one or more areas areas on the test surface.

45. An apparatus comprising:
an interferometer system configured to:
operate in a first mode to, for each of multiple areas of a test surface on a test object having different reflectivities, measure information about the reflectivity of the area over a range of angles and wavelengths;
operate in a second mode to interferometrically profile a topography of the test surface over a range including at least some of each of the multiple areas; and
correct the profile based on information about the reflectivity of the multiple areas to reduce errors.

46. The interferometry system of claim 45, wherein the test surface is a top surface of the test object.

47. The interferometry system of claim 45, wherein the test surface is a buried surface of the test object.

48. The interferometry system of claim 45, wherein the profile is a thickness profile.

49. The interferometry system of claim 45, wherein the interferometer system is configured to, for each area:
determine a height offset based on the information about the reflectivity of the area; and
add the offset to the corresponding portion of the profile.

50. The interferometry system of claim 45, wherein the interferometer system is configured to:
use the same interferometry system to measure information about the reflectivity of two or more reference surfaces over a range of angles and wavelengths; and
use information about the reflectivity of the two or more reference surfaces to determine information about the interferometry system; and
wherein the correcting of the profile is further based on the information about the interferometry system.

51. The interferometry system of claim 50, wherein the interferometer system is configured to:
determine additional information about the interferometer system based on the information about the reflectivity of the area over a range of angles and wavelengths; and
wherein the correcting of the profile is further based on the information about the interferometry system.

52. Use interferometry system of claim 45 further comprising: outputting the corrected profile.

53. The interferometry system of claim 45 wherein the outputting of the corrected profile comprises outputting to one of: a user, a display, electronic storage, an electronic controller, and electronic controller configured to operate one or more devices based on information related to the profile, printed media, and electronic storage media.

54. The interferometry system of claim 45 where the outputting of the corrected profile comprises outputting for use in semiconductor metrology measurements.

* * * * *

UNITED STATES PATENT AND TRADEMARK OFFICE
CERTIFICATE OF CORRECTION

| | | |
|---|---|---|
| PATENT NO. | : 7,619,746 B2 | Page 1 of 1 |
| APPLICATION NO. | : 11/780360 | |
| DATED | : November 17, 2009 | |
| INVENTOR(S) | : Xavier Colonna de Lega | |

It is certified that error appears in the above-identified patent and that said Letters Patent is hereby corrected as shown below:

On Cover Page, (12), delete inventor name "De Lega", insert --Colonna de Lega--.

On Cover Page, in (57) Abstract, line 6, delete "interferometry-system" and insert --interferometry system--.

Column 32, line 61, after "one of", insert --:--.

Column 34, line 45, delete "about," and insert --about--.

Column 35, line 6, delete "fight", insert --light--.

Column 35, line 36, delete "calibration," and insert --calibration--.

Column 36, line 4, in Claim 32, delete "in formation", insert --information--.

Column 36, line 48, delete "irons", insert --from--.

Column 36, line 67, delete second occurrence of "areas".

Column 38, line 14, delete "Use", insert --The--.

Signed and Sealed this

Nineteenth Day of January, 2010

David J. Kappos
*Director of the United States Patent and Trademark Office*